United States Patent

Ryono et al.

[11] Patent Number: 6,117,885
[45] Date of Patent: Sep. 12, 2000

[54] BIPHENYL-SUBSTITUTED QUINOLINE DERIVATIVES

[75] Inventors: Denis Evan Ryono, Princeton, N.J.; John Lloyd, Yardley, Pa.

[73] Assignee: E. R. Squibb & Sons, Inc., Princeton, N.J.

[21] Appl. No.: 08/200,985

[22] Filed: Feb. 24, 1994

Related U.S. Application Data

[63] Continuation of application No. 07/943,349, Sep. 10, 1992, abandoned, which is a continuation-in-part of application No. 07/837,782, Feb. 14, 1992, abandoned.

[51] Int. Cl.[7] .......................... A61K 31/47; C07D 215/50
[52] U.S. Cl. ..................... 514/312; 514/82; 514/300; 546/21; 546/23; 546/123; 546/156
[58] Field of Search ..................... 546/156, 23; 514/312, 514/82

[56] References Cited

U.S. PATENT DOCUMENTS

| | | | |
|---|---|---|---|
| 4,920,131 | 4/1990 | Huang et al. | 546/153 |
| 5,157,040 | 10/1992 | Greenlee et al. | 514/312 |
| 5,210,204 | 5/1993 | Connor et al. | 514/312 |
| 5,369,114 | 11/1994 | Roberts et al. | 514/312 |

FOREIGN PATENT DOCUMENTS 0191603  8/1986  European Pat. Off. ............... 514/313

*Primary Examiner*—Richard L. Raymond
*Attorney, Agent, or Firm*—Burton Rodney

[57] ABSTRACT

Compounds of the formula

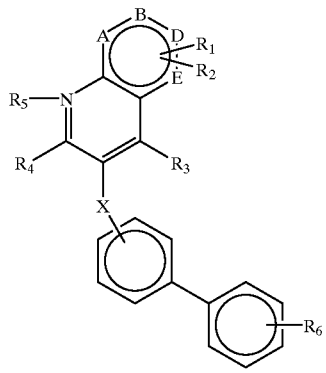

wherein X, $R_1$, $R_2$, $R_3$, $R_4$, $R_5$, $R_6$, A, B, D and E are as defined herein. These compounds inhibit the action of angiotensin II and are useful, therefore, for example, as antihypertensive agents.

41 Claims, No Drawings

BIPHENYL-SUBSTITUTED QUINOLINE DERIVATIVES

This is a continuation of application Ser. No. 07/943,349, filed Sep. 10, 1992, now abandoned, which is a continuation-in-part of U.S. Ser. No. 07/837,782, filed Feb. 14, 1992, now abandoned.

FIELD OF THE INVENTION

The present invention relates to novel substituted quinolines which are useful as antihypertensive agents.

SUMMARY OF THE INVENTION

In accordance with the present invention, novel compounds which inhibit the action of the hormone angiotensin II are disclosed. These compounds are of the general formula and pharmaceutically acceptable salts and prodrugs thereof.

As used in formula I, and throughout the specification, the symbols have the following meanings:

A, B, D and E are each carbon atoms or one of A, B, D and E is a nitrogen atom;

X is —O—, —CH$_2$—, —S—, —SO—, —SO$_2$—, —NH— or $$-\overset{O}{\underset{\|}{C}}-;$$

$R_1$ and $R_2$ are substituents on A, B, D or E when A, B, D or E are carbon and are independently selected from hydrogen; alkyl of 1 to 4 carbon atoms optionally substituted with substituents selected from amino, hydroxy or alkoxy of 1 to 4 carbon atoms; alkoxy of 1 to 4 carbon atoms, halogen; hydroxy; haloalkyl; cyano; nitro; amino; alkylamino or dialkylamino of up to 6 carbon atoms; (dialkylamino)alkyl of 3 to 8 carbon atoms; alkanoyl of 1 to 4 carbon atoms; carbamoyl; (N-alkyl)carbamoyl or di(N-alkyl)carbamoyl of up to 7 carbon atoms; carboxy; alkoxycarbonyl of 1 to 4 carbon atoms; alkylthio of 1 to 6 carbon atoms; alkylsulphinyl of 1 to 6 carbon atoms; alkylsulphonyl of 1 to 6 carbon atoms;

$R_3$ is —CO$_2$H, —CO$_2$R$_7$, —CH$_2$OH, —CHO, —CONHOR$_{10}$, —CONHR$_8$, —CONR$_8$R$_8$', —CONH$_2$ or —CONHSO$_2$CF$_3$;

$R_4$ is hydrogen, alkyl, alkenyl, alkynyl, arylalkyl, cycloalkyl, (cycloalkyl)alkyl, phenyl, or an alkyl substituted with 1 or more fluorine atoms;

$R_5$ is an optional oxygen atom;

$R_6$ is hydrogen, —CO$_2$R$_9$, —NHSO$_2$CF$_3$, —OS(OH)$_2$$\overset{O}{\underset{\|}{}}$, —SO$_3$H, —C(CF$_3$)$_2$OH, —OP(OH)$_2$$\overset{O}{\underset{\|}{}}$, —PO$_3$H$_2$, —NHP(OH)$_2$$\overset{O}{\underset{\|}{}}$, —CONHSO$_2$CF$_3$, [tetrazole], —CH$_2$—[tetrazole], [triazole-CF$_3$], —CONH—[tetrazole], —CONHOR$_{10}$,

[tetrazole]—CH(R$_{10}$)—O—COR$_{11}$, [tetrazole]—CH(R$_{10}$)—O—COOR$_{11}$, $-\overset{OH}{\underset{R_{12}}{C}}-\overset{O}{\underset{\|}{P}}(OH)_2$ or [triazole-R$_{13}$];

$R_7$ is alkyl, aryl, arylalkyl, aryloxyalkyl, —CH$_2$—COOR$_8$, —CH$_2$CONR$_8$R$_8$', —CH(R$_{10}$)—O—COR$_{11}$, —CH(R$_{10}$)—O—COR$_{11}$ or indanyl;

$R_8$ and $R_8$' are independently a lower alkyl;

$R_9$ is hydrogen, alkyl, perfluoroalkyl of 1 to 8 carbon atoms, cycloalkyl of 3 to 6 carbon atoms, phenyl, benzyl, —CH(R$_{10}$)—O—COR$_{11}$ or —CH(R$_{10}$)—O—COOR$_{11}$;

$R_{10}$ is hydrogen, alkyl, aryl, arylalkyl or cycloalkyl;

$R_{11}$ is alkyl, aryl, alkylaryl, arylalkyl or cycloalkyl;

$R_{12}$ is hydrogen, alkyl of 1 to 5 carbon atoms or phenyl; and $R_{13}$ is —CN, —NO$_2$ or —CO$_2$R$_9$.

DETAILED DESCRIPTION OF THE INVENTION

The present invention relates to the compounds of formula I, to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" or "halo" refers to fluorine, chlorine, bromine and iodine with fluorine and chlorine being preferred.

The term "haloalkyl" refers to such alkyl groups described above in which one or more hydrogens have been replaced by chlorine, bromine or fluorine, such as trifluoromethyl, pentafluoroethyl, 2,2,2-trichloroethyl, chloromethyl, bromomethyl, with trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. Preferred aryl groups are phenyl and monosubstituted phenyl and phenyl is most preferred.

The term "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms. Preferred monocyclic heterocyclo groups include 2- and 3-thienyl, 2- and 3-furyl, 2-, 3- and 4-pyridyl, and imidazolyl. The heterocycle may also have a substituent selected from alkyl of 1 to 4 carbons, carboxy, alkoxy of 1 to 4 carbons and alkylthio of 1 to 4 carbons on an available carbon. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranyl. Preferred fused heterocycles include thienyl, furyl, pyridyl and imidazolyl, optionally substituted as described above.

The term "substituted amino" refers to a group of the formula —$NZ_1Z_2$ wherein $Z_1$ is hydrogen, alkyl, or aryl-($CH_2$) p— and $Z_2$ is alkyl or aryl-($CH_2$) p— or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

It should be understood that the present invention includes prodrug forms, such as ester, particularly (5-substituted 2-oxo-1,3-dioxo-len- 4-yl)methyl esters such as those of the structure:

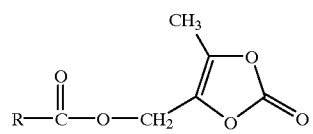

(F. Sakamoto, S. Ikeda, G. Tsukamoto, *Chem Pharm Bull*, vol. 32, pp.2241–2248, 1984), acetal and/or mixed acetal derivatives of the compounds of formula I. For example, such derivatives have been documented in *Design of Prodrugs*, edited by H. Bundgard, (Elsevier, 1985) and *Methods in Enzymology*, Vol. 42, p. 309–396, edited by K. Widder et al. (Academic Press, 1985). Further, it is understood that any moiety at $R_3$ and/or $R_6$ that will be cleaved in vivo to provide an acidic $R_3$ and/or $R_6$ moiety is within the spirit and scope of this invention.

An examplary process for preparing the compounds of formula I where A, B, D and E are carbon atoms, $R_1$ and $R_2$ are hydrogen and X is oxygen includes reacting a phenol of the formula

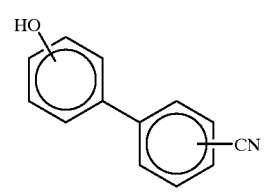

II with a haloketone of the formula

III where hal is a halogen, in the presence of a base such as potassium carbonate, to form ketones of the formula

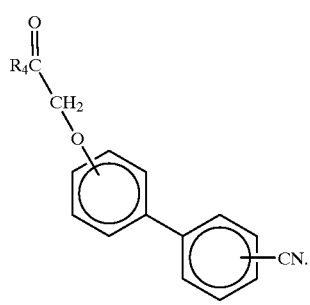

IV

Compounds of formula IV are then reacted with an optionally substituted isatin (such as those disclosed in "Advances in Heterocyclic Chemistry", Ed. A. R. Katritzky, A. J. Boulton, Vol. 18, chapter authored by F. D. Popp, p. 1–58, (1975)) in water (or water plus an organic co-solvent such as ethanol) in the presence of a base such as potassium hydroxide to form amides of the formula

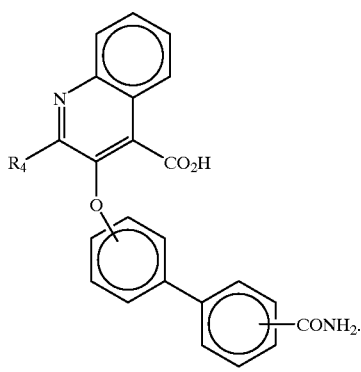

V

The compounds of formula V are then reacted with a dehydrating agent such as trifluoroacetic anhydride in an organic solvent such as dioxane in the presence of a base such as pyridine to form compounds of formula

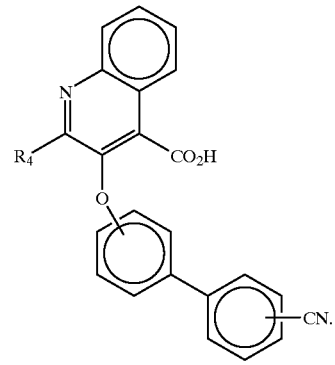

VI

Compounds of formula VI are then reacted with an azide such as tributyltin azide in an organic solvent such as xylene to form the compounds of formula I where $R_6$ is 5-tetrazolyl.

Alternatively, compounds of formula IV may be reacted with an azide such as tributyltin azide to form compounds of formula

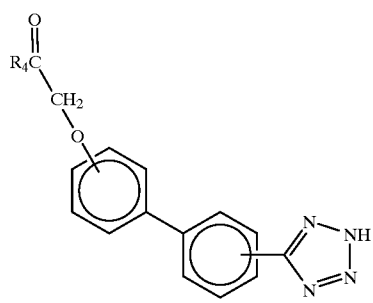

IVA

Compounds of formula IVA can be reacted with an optionally substituted isatin in water in the presence of a base such as potassium hydroxide to form compounds of formula I where $R_6$ is 5-tetrazolyl.

Compounds of the formula II are prepared by reaction of compounds of the formula

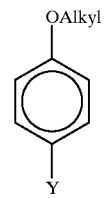

VII where Y is bromine or chlorine, with an alkyllithium such as butyllithium followed by a zinc salt such as zinc chloride in an organic solvent such as tetrahydrofuran to give compounds of the formula

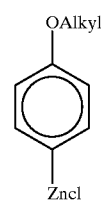

VIII which are then reacted with an arylhalide such as 2-bromobenzonitrile in the presence of a catalyst such as tetrakis(triphenylphosphine)palladium(O) to form compounds of the formula

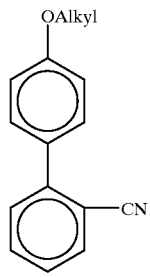

IX which are then reacted with an acid such as boron tribromide in an organic solvent such as methylene chloride.

Compounds of formula III may be prepared by reacting a compound of formula

X with diazomethane to form an intermediate diazoketone which is converted to compounds of formula III by reaction with dry gaseous H-hal.

An exemplary process for preparing compounds of the formula I where A, B, D are carbon atoms and E is a nitrogen atom, $R_1$ and $R_2$ are hydrogen and X is oxygen includes reacting a ketone of the formula IV with a compound of the formula

XI or

XIA in water (or water plus an organic co-solvent such as ethanol) in the presence of a base such as potassium hydroxide to form amides of the formula

XII

The compounds of formula XII are then reacted with a dehydrating agent such as trifluoroacetic anhydride in an organic solvent such as dioxane in the presence of a base such as pyridine to form compounds of the formula

XIII

Compounds of the formula XIII are then reacted with an azide such as tributyltin azide in an organic solvent such as xylene to form compounds of the formula I where $R_6$ is 5-tetrazolyl and E is a nitrogen atom.

Alternatively, compounds of the formula I where A, B, D are carbon and E is nitrogen and $R_1$ and $R_2$ are hydrogen may be prepared by reaction of a compound of the formula IVA with a compound of the formula XIA in water (or water plus an organic cosolvent such as ethanol) in the presence of a base such as potassium hydroxide to form compounds of the formula I where $R_6$ is 5-tetrazolyl and E is nitrogen.

A compound of the formula XI or XIA is prepared by reaction of a compound of the formula

XIV (synthesis of XIV is described by Finch, N; Robinson, M. M.; Valerio, M. P., *Journal of Organic Chemistry* (1972), Vol. 37, pp 51–54) with a brominating agent such as N-bromosuccinimide in a solvent such as t-butanol to form a compound of the formula

XV

A compound of the formula XV may be hydrolyzed to a compound of the formula XI by reaction with a silver salt such as silver trifluoroacetate in an organic solvent such as acetonitrile followed by reaction with water.

An exemplary process for preparing compounds of the formula I where A is a nitrogen atom B, D and E are carbon atoms, $R_1$ and $R_2$ are hydrogen and X is oxygen includes reacting a ketone of the formula IV with a compound of the formula

XVI or

XVIA in water (or water plus an organic co-solvent such as ethanol) in the presence of a base such as potassium hydroxide to form amides of the formula

XVII

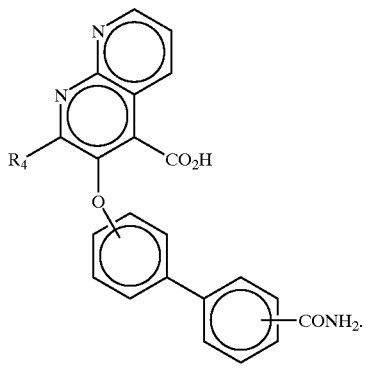

The compounds of the formula XVII are then reacted with a dehydrating agent such as trifluoroacetic anhydride in an organic solvent such as dioxane in the presence of a base such as pyridine to form compounds of the formula

XVIII

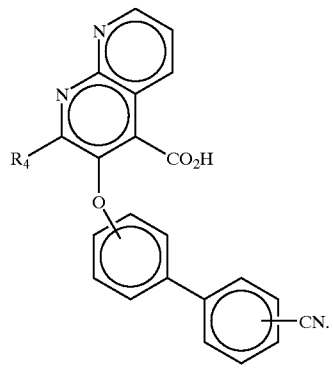

Compounds of the formula XVIII are then reacted with an azide such as tributyltin azide in an organic solvent such as xylene to form compounds of the formula I where $R_6$ is 5-tetrazolyl and A is a nitrogen atom.

Alternatively, compounds of the formula I where A is nitrogen and B, D, E are carbon and $R_1$ and $R_2$ are hydrogen may be prepared by reaction of a compound of the formula IVA with a compound of the formula XVIA in water (or water plus an organic cosolvent such as ethanol) in the presence of a base such as potassium hydroxide to form compounds of the formula I where $R_6$ is 5-tetrazolyl and A is nitrogen.

The compound of the formula XVI is prepared by reaction of a compound of the formula

XIX

with a brominating agent such as pyridinium bromide perbromide (as described by Marfat, A; Carta, M. P.; *Tetrahedron Letters* (1987), Vol. 28, pp 4027–4030) to form a compound of the formula

XX

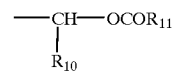

A compound of the formula XX can then be hydrolyzed to a compound of the formula XVI or XVIA by reaction with a silver salt such as silver trifluoroacetate in an organic solvent such as acetonitrile followed by reaction with water.

An exemplary process for preparing a compound of the formula I where $R_3$ is —$CO_2R_7$ and $R_7$ is $$-\underset{R_{10}}{\underset{|}{CH}}-OCOR_{11}$$

includes reacting a compound of the formula I where $R_6$ is 5-tetrazoyl and $R_3$ is —$CO_2H$ with triphenylchloromethane in the presence of a base such as triethylamine in a solvent such as acetone to form compounds of the formula

XXI

Compounds of the formula XXI can then be reacted with a compound of the formula

XXII $$Y\underset{R_{10}}{\underset{|}{\diagdown}}O\underset{O}{\overset{\diagup}{\diagdown}}R_{11}$$

where Y is halogen, in an organic solvent such as dimethylformamide with a base such ascesium carbonate to form compounds of the formula

XXIII

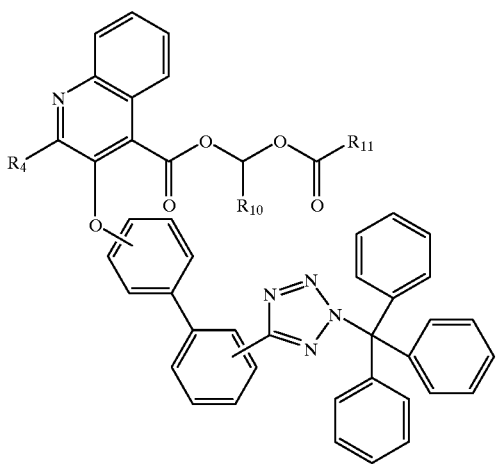

Compounds of the formula XXIII can then react with an acid such as aqueous hydrochloric acid in a solvent such as tetrahydrofuran to give compounds of the formula I where $R_6$ is 5-tetreazoyl.

Compounds of the formula XXII can be made by reacting an alkyl acid chloride such as propionylchloride with a zinc salt such as zinc chloride in an organic solvent such as methylene chloride followed by addition of an alkyl aldehyde such as isobutyraldehyde.

An exemplary process for preparing compounds of the formula I where A, B, D and E are carbon atoms, $R_1$ and $R_2$ are hydrogen, $R_6$ is 5-tetrazolyl, and X is sulfur includes reacting a thiophenol of the formula

XXIV

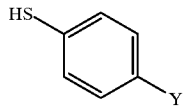

where Y is bromine or chlorine with methyl iodide in the presence of a base such as potassium carbonate in a solvent such as dimethylformamide to form the product of formula

XXV

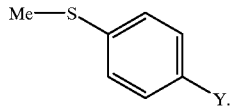

Compounds of the formula XXV are then reacted with an alkyllithium such as butyllithium followed by a zinc salt such as zinc chloride in an organic solvent such as tetrahydrofuran to give compounds of the formula

XXVI

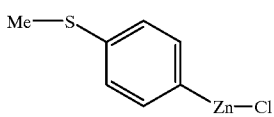

which are then reacted with an aryl halide such as 2-bromobenzonitrile in the presence of a catalyst such as tetrakis(triphenylphosphine)palladium(O) to form compounds of the formula

XXVII

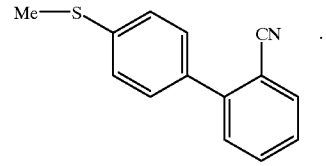

Compounds of the formula XXVII are then reacted sequentially with an oxidizing agent such as m-chloroperbenzoic acid, followed by an anhydride such as trifluoroacetic anhydride, and finally by a solution of triethylamine in methanol to provide products of the formula

XXVIII

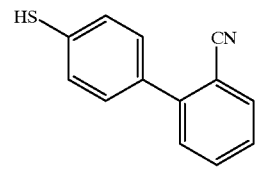

(procedure described in R. N. Young, J. Y. Gauthier, and W. Coombs, *Tetrahedron Lett.* (1984), Vol. 25, 1753).

Compounds of formula XXVIII are then reacted with a haloketone of formula III in the presence of a base such as potassium carbonate in a solvent such as dimethylformamide to form arylthioketones of the formula

XXIX

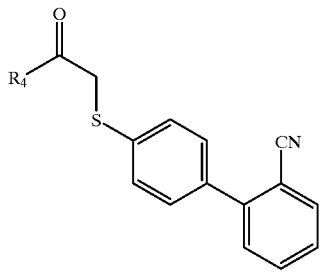

which may be reacted with a trialkyltin azide reagent such as tri-n-butyltin azide to form tetrazole ketone products of the formula

XXX

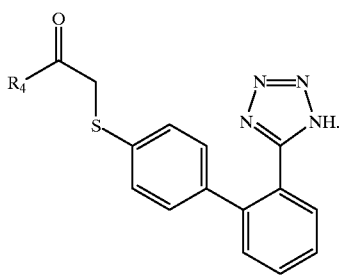

Compounds of formula XXX are then reacted with an optionally substituted isatin (such as those disclosed in "Advances in Heterocyclic Chemistry" Ed. A. R. Katritsky, A. J. Boulton, Vol. 18, chapter authored by F. D. Popp. pp. 1–58, (1975)) in water (or water plus an organic cosolvent such as ethanol) in the presence of a base such as potassium hydroxide to form compounds of the formula

XXXI

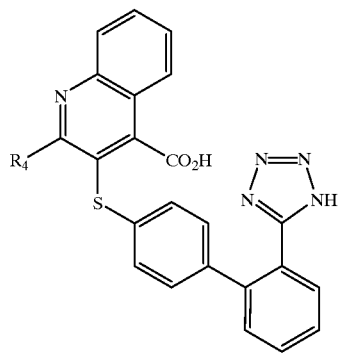

a-Arylthio substituted ketones have previously been shown to undergo the Pfitzinger quinoline synthesis (Badische Anilin- und Soda-Fabrik, Ger. Pat. 335,197; *Chem. Abstr.* (1923), Vol. 17, 1802).

For the preparation of compounds of the formula I in which X is —SO— (a sulfoxide functional group), the procedure for the preparation of compounds of the formula XXXI may be followed except that the compound of the formula XXX is substituted by the compound of formula

XXXII

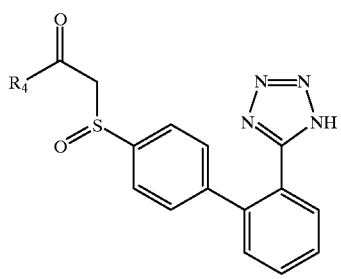

which may be prepared by treatment of the compound of formula XXX with one equivalent of an oxidizing agent such as meta-chloroperbenzoic acid.

For the preparation of compounds of the formula I in which X is —SO$_2$— (a sulfone functional group), the procedure for the preparation of compounds of the formula XXXI may be followed except that the compound of the formula XXX is substituted by the compound of formula

XXXIII

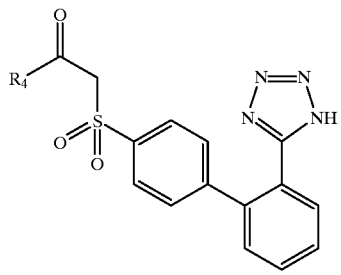

which may be prepared by treatment of the compound of formula XXX with two equivalents of an oxidizing agent such as meta-chloroperbenzoic acid.

An exemplary process for preparing the compounds of formula I where A, B, D and E are carbon atoms, $R_1$ and $R_2$ are hydrogen, $R_6$ is 5-tetrazolyl, and X is N—H includes reacting an amine of the formula

XXXIV

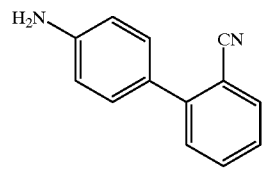

with a haloketone of the formula III where hal is a halogen, in the presence of a base such as potassium carbonate, in an organic solvent such as N,N-dimethylformamide, to form ketones of the formula

XXXV

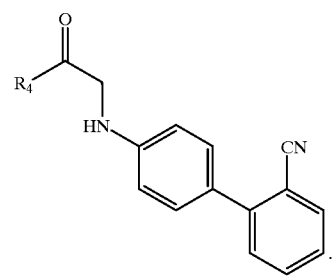

Compounds of the formula XXXV may then react with an azide such as tri-n-butyltin azide in an organic solvent such as xylene to form compounds of the formula

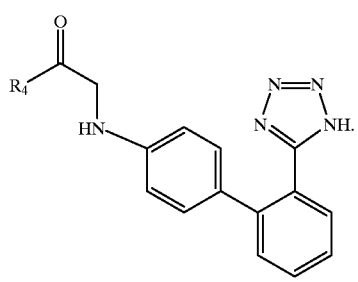
XXXVI

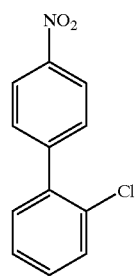
XXXIX which may then be reduced using a reducing agent such as hydrogen with a catalyst such as 10% palladium on carbon in an organic solvent such as ethyl acetate to prepare compounds of the formula XXXIV.

Compounds of formula XXXVI are then reacted with an optionally substituted isatin (such as those disclosed in "Advances in Heterocyclic chemistry", Ed. A. R. Katritsky, A. J. Boulton, Vol. 18, chapter authored by F. D. Popp. pp. 1–58, (1975)) in water (or water plus an organic cosolvent such as ethanol) in the presence of a base such as potassium hydroxide to form compounds of the formula I were X is N—H and $R_6$ is 5-tetrazolyl. a-Amino ketones have previously been demonstrated to undergo the Pfitzinger quinoline synthesis (H. De Diesbach, E. Moser *Hely. Chim. Acta* (1937), Vol. 20, 132).

An exemplary process for preparing the compounds of formula I where A, B, D and E are carbon atoms, $R_1$ and $R_2$ are hydrogen, $R_6$ is tetrazolyl, and X is —CO— includes reacting a bromide of the formula

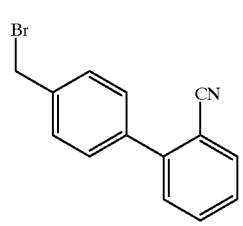
XL

Compounds of the formula XXXIV may be prepared by reaction of compounds of the formula

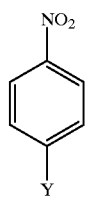
XXXVII with dimethyl sulfoxide in the presence of a base such a sodium bicarbonate to form an aldehyde of the formula

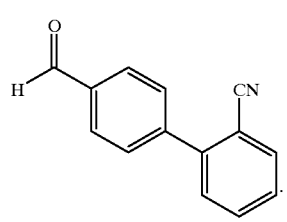
XLI where Y is bromine or chlorine, with an alkyllithium such as n-butyllithium followed by a zinc salt such as zinc chloride in an organic solvent such as tetrahydrofuran to give compounds of the formula

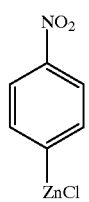
XXXVIII

The bromide of formula XL is prepared by procedures described in (D. J. Carini et al., *J. Med. Chem.* (1991), Vol. 34, 2525).

A compound of the formula XLI is reacted with a ketone of the formula $R_4$—CO—CH$_3$  XLII which are then reacted with an aryl halide such as 2-bromobenzonitrile in the presence of a catalyst such as tetrakis(triphenylphosphine)palladium(O) to form compounds of the formula in the presence of a base such as lithium diisopropyl amide, in an organic solvent such as tetrahydrofuran, to form ketones of the formula

XLIII

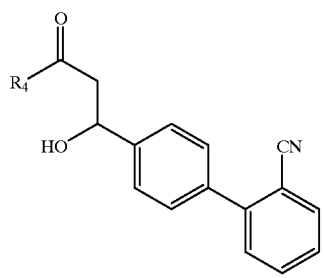

which may then be protected by reaction with chloromethylmethyl ether in the presence of a base such as diisopropylethyl amine in an organic solvent such as dichloromethane to produce compounds of the formula

XLIV

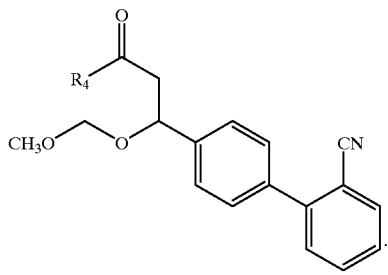

Compounds of the formula XLIV are then reacted with an azide such as tri-n-butyltin azide in an organic solvent such as xylene to form compounds of the formula

XLV

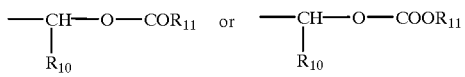

Compounds of formula XLV are then reacted with an optionally substituted isatin (such as those disclosed in "Advances in Heterocyclic chemistry" Ed. A. R. Katritsky, A. J. Boulton, Vol. 18, chapter authored by F. D. Popp. pp. 1–58, (1975)) in water (or water plus an organic cosolvent such as ethanol) in the presence of a base such as potassium hydroxide to form compounds of the formula

XLVI

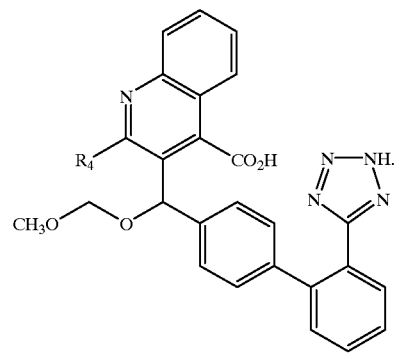

Compounds of the formula XLVI are then reacted with an acid such hydrochloric acid in an organic solvent such as methanol to form compounds of the formula

XLVII

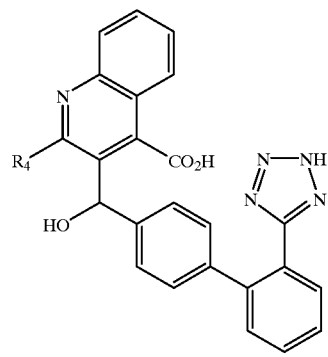

which can be oxidized using an oxidizing agent such as dimethylsulfoxide and oxalyl chloride in the presence of a base such as diisopropylethyl amine in an organic solvent such as dichloromethane to form compounds of the formula I were X is —CO— and $R_6$ is 5-tetrazolyl.

To prepare compounds of formula I where A, B, D and E are carbon atoms, $R_1$ and $R_2$ are hydrogen, $R_6$ is 5-tetrazolyl, and X is —$CH_2$—, the alcohol of formula XLVII is treated with a reducing agent such as hydrogen in the presence of a catalyst such as 10% palladium on carbon.

Preferred compounds of the present invention are those wherein $R_1$ and $R_2$ are independently hydrogen, methyl, methoxy, chlorine or bromine;

$R_3$ is —COOH, —$COOR_7$ where $R_7$ is ethyl, propyl, butyl, $$—\underset{\underset{R_{10}}{|}}{CH}—O—COR_{11} \quad \text{or} \quad —\underset{\underset{R_{10}}{|}}{CH}—O—COOR_{11}$$

where $R_{10}$ and $R_{11}$ are independently methyl, ethyl, isopropyl or t-butyl;

$R_4$ is methyl, ethyl, propyl, butyl, pentyl, cyclopropyl, trifluoromethyl, or pentafluoroethyl;

$R_5$ is absent or is oxygen;
$R_6$ is 5-tetrazolyl,

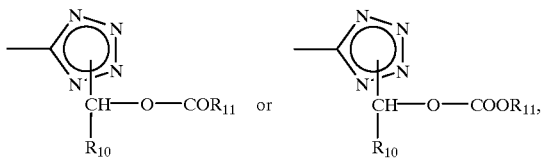

where
$R_{10}$ and
$R_{11}$ is defined as above;
X is oxygen, sulfur or $-SO_2$; and
A, B, D and E are all carbon, or A or E is nitrogen.
Most preferred are compounds of formula I wherein
$R_1$ and $R_2$ are independently hydrogen, bromine or chlorine;
$R_3$ is $-COOH$ or $-COOR_7$ where $R_7$ is

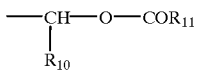

where
$R_{10}$ is methyl, ethyl, t-butyl or isopropyl;
$R_4$ is methyl, ethyl, propyl or cyclopropyl;
$R_5$ is absent or is oxygen;
$R_6$ is 5-tetrazolyl;
x is oxygen; and
A, B, D and E are all carbon, or A, B, and D are carbon, and E is nitrogen.

The preferred prodrug forms of the compounds of formula I are the ester forms, particularly (5-substituted 2-oxo-1,3-dioxolen-4-yl)methyl ester.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

2-Propyl-3-[[2'-(2H-tetrazol-5-yl)[1,1'-biphenyl]-4-yl]oxy]-4-quinolinecarboxylic acid, dilithium salt A. 1-Chloro-2-pentanone Butyryl chloride (10 mL, 97 mmol) was dissolved in dry diethylether (100 mL) and cooled to 0° C. A solution of diazomethane (194 mmol) in ether was added and the reaction was allowed to stand at −10° C. for 16 hours. The bright yellow solution was then treated with hydrogen chloride gas and the color was discharged. The ether was removed and the residue distilled in vacuo (50° C.–56° C./10–15 mm Hg) to yield the title compound as a colorless liquid (7.4 g, 64%).

B. 4'-Hydroxy[1,1'-biphenyl]-2-carbonitrile

To a solution of 4-bromoanisole (18.7 g, 0.1 mol) in anhydrous tetrahydrofuran (200 mL) at −78° C. was added a solution of n-BuLi (2.5M solution, 40 mL) in hexane. After stirring for 30 minutes, a solution of zinc chloride (1M solution, 100 mL) in ether was added. After the mixture was stirred for one hour at −78° C., Pd(Ph$_3$P)$_4$ (0.85 g, 0.73 mmol) and 2-bromobenzonitrile (18.2 g, 0.1 mol) were added. The reaction mixture was stirred at room temperature overnight, and then was concentrated in vacuo. The residue was partitioned between ethyl acetate (400 mL) and 1N hydrochloric acid (100 mL). The organic solution was washed with brine and dried over magnesium sulfate. Concentration in vacuo gave a crude intermediate 4'-methoxy [1,1'-biphenyl]-2-carbonitrile, which was directly used for the next step (the compound can be triturated with ether to obtain a pure solid product). To a solution of the crude intermediate in methylene chloride (150 mL) at −78° C. was added boron tribromide (1M solution, 200 mL) in methylene chloride. After the addition, the resulting solution was stirred at room temperature overnight. The reaction was quenched by adding very slowly methanol (100 mL) at −78° C. The mixture was then poured into ice water. Ethyl acetate (300 mL) was added to the aqueous mixture, the organic layer was washed with water and dried over magnesium sulfate. Concentration in vacuo gave a solid, which was triturated with ether to obtain the title compound (11.5 g, 59% overall). If needed, the product can also be purified by silica gel column eluting with toluene/ethyl acetate (4:1); m.p. 177–178° C.

C. 4'-(2-Oxopentyloxy)[1,1'-biphenyl]-2-carbonitrile

Potassium iodide (30 mg, 0.17 mmol) was dissolved in acetone (1.5 mL). The title A compound (185 mg, 1.54 mmol) was added followed by the title B compound (200 mg, 1.02 mmol) and potassium carbonate (212 mg, 154 mmol). The brown reaction mixture was then heated to 50° C. for 6.5 hours then allowed to stir at room temperature for an additional 16 hours. The mixture was then adsorbed onto silica gel and purified by flash chromatography on silica gel eluted with 5% acetone, 45% toluene, 50% hexane, to provide the title compound as a brown oil (260 mg, 91%).

D. 3-[[2'(Aminocarbonyl)[1,1'-biphenyl]-4-yl]oxy]-2-propyl-4-quinolinecarboxylic acid The title C compound (120 mg, 0.43 mmol) was suspended with potassium hydroxide (1.1 mL, 30% aq.) and isatin (63 mg, 0.43 mmol) was added and the reaction was heated to 105° C. for eight hours. The mixture was then acidified with hydrochloric acid and extracted with ethyl acetate. The organic extracts were combined, dried over magnesium sulfate and the solvent removed. The residue was purified by flash chromatography on silica gel eluted with 5% acetic acid, 20% acetone, 75% toluene to yield the title compound as a yellow solid (111 mg, 61%); m.p. 230° C.

E. 3-[(2'-Cyano[1,1'-biphenyl]-4-yl)oxy]-2-propyl-4-quinolinecarboxylic acid

The title D compound (103 mg, 0.24 mmol) was dissolved in dioxane (1.3 mL) and trifluoroacetic anhydride (68 µL, 0.48 mmol) and pyridine (59 mL, 0.73 mmol) were added. The mixture was stirred for 25 hours at room temperature. Additional trifluoroacetic anhydride was added after 20 hours (17 µL; 0.12 mmol) and after 23 hours (10 µL, 0.071 mmol). The reaction was quenched with hydrochloric acid (1.0 N aq.) and extracted with ethyl acetate. The organic extracts were combined, dried over magnesium sulfate and the solvent removed to yield the title compound as a solid (91 mg, 93%).

F. 2-Propyl-3-[[2'-(2H-tetrazol-5-yl)[1,1'-biphenyl]-4-yl]oxy]-4-quinolinecarboxylic acid, dilithium salt The title E compound (85 mg, 0.21 mmol) was suspended in p-xylene (400 µL), tributyltin azide (H. R. Kricheldorf, E. Leppert, *Synthesis*, 329 (1976)) (242 mg, 0.73 mmol) was added and the reaction was heated to 110° C. for 72 hours. The brown reaction mixture was cooled to room temperature and stirred with methanol for 30 minutes. The mixture was then adsorbed onto 2 g of silica gel and purified by flash chromatography on 25 g of silica gel eluted with 5% acetic acid, 25% acetone, 70% toluene to provide 65 mg of a pale yellow solid. This material was dissolved in a mixture of 800 µL lithium hydroxide (1.0 N aq.), 800 gL water and 400 µL methanol and purified by column chromatography using HP20 polystyrene resin (20 mL column volume) eluted with 50 mL each of water, 5% aqueous acetone and 10% aqueous acetone. The product containing fractions were combined and lyophilized to yield the lithium salt as a white solid (50 mg, 53%); m.p. >2700.

Elemental Analysis for $C_{26}H_{19}N_5O_3Li_2 \cdot 3.57 H_2O$
Calc'd: C 59.18; H 4.99; N 13.27;
Found: C 59.21; H 4.78; N 13.10.

EXAMPLE 2

2-Ethyl-3-[[2'-(2H-tetrazol-5-yl)[1,1'-biphenyl]-4-yl]oxy]-4-quinolinecarboxylic acid, dilithium salt A. 4'-(2-Oxobutyloxy)[1,1'-biphenyl]-2-carbonitrile A mixture containing the title B compound of Example 1 (3 g, 15.4 mmol) 1-bromo-2 butanone (3.47 g, 23 mmol), and cesium carbonate (10 g, 30.7 mmol) in dimethylformamide (22 mL) was heated at 50° C. overnight in a stoppered flask. Most of the dimethylformamide was removed by concentration in vacuo. The product was extracted into ethyl ether which was rinsed with water and brine, dried (magnesium sulfate), and concentrated in vacuo to obtain the crude product (5 g). Purification by flash chromatography on Merck silica gel (180 g), eluted with 6:1, hexanes:ethyl acetate afforded the title compound as a yellow oil (1.74 g, 43%).

B. 3-[[2' (Aminocarbonyl)[1,1'-biphenyl]-4-yl]oxy]-2-ethyl-4-quinolinecarboxylic acid A mixture of the title A compound (1.55 g, 5.84 mol) and isatin (860 mg, 5.84 mmol) in aqueous potassium hydroxide (15 mL, 30%) was heated at 105° C. for 4.5 hours in a stoppered flask. The cooled reaction was then acidified with 1N aqueous hydrochloric acid and extracted with ethyl acetate. The organic extract was rinsed with water and brine, dried (magnesium sulfate) and concentrated in in vacuo to yield a crude title compound (2.12 g, 88%).

C. 3-[(2'-Cyano[1,1'-biphenyl]-4-yl)oxy]-2-ethyl-4-quinolinecarboxylic acid

The crude title B compound (2.12 g, nominally 5.14 mmol) was dissolved in a mixture of dioxane (12.8 mL) and pyridine (6.4 mL). Under an argon atmosphere the solution was cooled in an ice-bath and treated with trifluoroacetic anhydride (3.2 mL). The cold bath was removed and the reaction kept at ambient temperature for 2.5 hours, the poured into a stirred mixture of 1N aqueous hydrochloric acid (150 mL) and ethyl acetate (150 mL). The organic layer was separated and the aqueous solution was further extracted with ethyl acetate. The combined organic extracts were rinsed with 1N hydrochloric acid (50 mL) and 5:1 (v:v) water:brine (60 mL), and brine (150 mL), then dried (magnesium sulfate) and concentrated in vacuo to afford the crude product. Flash chromatography on Merck silica gel (140 g) eluted with 5:4:0.1 hexanes:ethyl acetate:acetic acid gave the title compound (0.98 g, 48%).

D. 2-Ethyl-3-[[2'-(2H-tetrazol-5-yl)[1,1'-biphenyl]-4-yl]oxy]-4-quinolinecarboxylic acid, dilithium salt A mixture of the title C compound (300 mg, 0.761 mmol), tributyltin azide (1.01 g, 3.04 mmol) and xylenes (0.5 mL) was heated at 100° C. in a stoppered flask for 18 hours, then treated with additional tributyltin azide (0.5 g) and re-heated for another 24 hours. At the end of that time an additional 0.1 g of the azide reagent was added to the reaction mixture and heating was continued overnight. After cooling to room temperature, the reaction was treated with methanol (2 mL), stirred for 30 minutes, and concentrated in vacuo to obtain the crude product tetrazole. The crude material was purified by flash chromatography (silicon dioxide, 75:20:5 toluene:acetone:acetic acid) to provide a purified tetrazole (title compound, 290 mg). Lithium hydroxide (1.6 mL, 1.0M) was then added to the tetrazole and water (6 mL) and methanol (1 mL) were added in order to effect a solution. The solution was then placed on an HP-20 column (60 mL) and chromatographed, eluting with water (500 mL), then 250 mL each of 5–15% acetone:water in 5% increments. The product was concentrated, passed through a millipore filter and lyophilized to provide the purified product (258 mg, 75%); m.p.>270° C.

Elemental Analysis for $C_{25}H_{17}N_5O_3Li_2.3.47\ H_2O$
Calc'd: C 58.67; H 4.71; N 13.68;
Found: C 58.33; H 4.21; N 13.36.

EXAMPLE 3

2-Propyl-3-[2'-(2H-tetrazol-5-yl)[1,1'-biphenyl]-4-yl]oxy]-4-quinolinecarboxylic acid, ethyl ester, monolithium salt A. 3-(2'-Cyano[1,1'-biphenyl]-4-yloxy)-2-propyl-4-quinolinecarboxylic acid, ethyl ester The title E compound of Example 1 (0.320 g, 0.783 mmol) and freshly ground cesium carbonate (0.640 g, 1.96 mmol) were stirred in anhydrous dimethylformamide (1.6 mL). Iodoethane (0.244 g, 1.57 mmol) was added and the reaction was stirred at room temperature for 18 hours. The reaction was then partitioned between ethyl acetate and water, making the aqueous phase acidic by the addition of 1N hydrochloric acid. The organic phase was dried and concentrated to provide the crude ethyl ester (0.395 g, 100%), which was used in the next step without any further purification.

B. 2-Propyl-3-[2'-(2H-tetrazol-5-yl)[1,1'-biphenyl]-4-yl]oxy]-4-quinolinecarboxylic acid, ethyl ester The title A compound (0.341 g, 0.781 mmol) and tri-n-butyltin azide (1.05 g, 3.1 mmol) were combined in anhydrous xylene and heated at 100° C. for 96 hours. The reaction was then concentrated and was purified by flash chromatography on silica gel eluting with hexane:ethyl acetate:acetic acid (75:20:5) to provide the title compound (0.370 g, 99%).

C. 2-Propyl-3-[2'-(2H-tetrazol-5-yl)[1,1'-biphenyl]-4-yl]oxy]-4-quinolinecarboxylic acid, ethyl ester, monolithium salt 0.1M Lithium carbonate (5.0 mL, 0.5 mmol) was added to the title B compound and methanol (5.0 mL) was added to effect a solution. The reaction was then concentrated to approximately 5.0 mL and was chromatographed through an HP-20 column using 300 mL each of 0–40% acetone:water in 10% increments of increasing acetone. The product was concentrated to approximately 50 mL and was passed through a millipore filter and lyophilized to provide the title compound as a white solid (0.247 g, 66%). m.p. 175° C. to 185° C.

Elemental Analysis for $C_{28}H_{24}N_5O_3.Li.1.75\ H_2O$
Calc'd: C 65.05; H 5.36; N 13.55;
Found: C 65.33; H 5.03; N 13.25.

EXAMPLE 4

2-Propyl-3-[2'-(2H-tetrazol-5-yl)[1,1'-biphenyl]-4-yl]oxy]-4-quinolinecarboxylic acid, ethyl ester, 1-oxide, monolithium salt The title compound of Example 3 (0.102 g, 0.197 mmol) was dissolved in methylene chloride (10.0 mL) and then 3-chloroperoxybenzoic acid (0.074 g, 0.43 mmol) was added at room temperature. The reaction was then stirred at room temperature for two hours and then heated to 35° C. for another two hours. The reaction was then cooled and partitioned between 1N hydrochloric acid and methylene chloride and the organic phase was dried and concentrated. The crude material was preabsorbed on silica gel and was flash chromatographed on silica gel, eluting with hexane:ethyl acetate:acetic acid (65:30:5) to provide purified N-oxide (69.3 mg, 71%). The purified material was then combined with the same material (30 mg) which was purified previously and suspended in 0.1M aqueous lithium carbonate (2.0 mL). Water (1.0 mL) and methanol (1.0 mL) were added in order to effect a solution. The solution was stirred for 15 minutes and then was chromatographed through an HP-20 column, eluting with water (200 mL) and then 100 mL each of 5–40% acetone:water in 5% increments. The product was concentrated, passed through a millipore filter and lyophilized to provide the lithium salt (67 mg, 70%); m.p. 187–200° C.

Elemental Analysis for $C_{28}H_{24}N_5O_4.Li.2.75\ H_2O$
Calc'd: C 61.03; H 5.40; N 12.71;
Found: C 61.33; H 5.02; N 12.41.

EXAMPLE 5

2-Propyl-3-[2'-(2H-tetrazol-5-yl)[1,1'-biphenyl]-4-yl]oxy]-4-quinolinecarboxylic acid, 2-methyl-1-(1-oxopropoxy)propyl ester, monolithium salt A. Propanoic acid, 1-chloro-2-methylpropyl ester To freshly fused zinc chloride (41 mg) in methylene chloride (10 mL) was added propionyl chloride (5.0 g, 54.0 mmol). The reaction was cooled to 10° C. and isobutyraldehyde (3.89 g, 54.0 mmol) was added dropwise maintaining the temperature at 25° C. Once the addition was complete, the reaction was stirred for one hour at room temperature. The reaction mixture was washed with 20% sodium acetate and the organic phase was concentrated in vacuo to provide product of sufficient purity.

B. 3-(2'-Cyano[1,1'-biphenyl]-4-yl]oxy)-2-propyl-4-quinolinecarboxylic acid, 2-methyl-1-(1-oxopropoxy)propyl ester, monolithium salt The title E compound of Example 1 (600 mg, 1.47 mmol) was dissolved in N,N-dimethylformamide (5 mL). The title A compound (846 mg, 5.14 mmol), cesium carbonate (1.68 g, 5.14 mmol) and sodium iodide (770 mg, 5.14 mmol) were added and the reaction was heated to 90° C. for five hours. Another addition of the chloride (545 mg, 3.31 mmol) was made and the reaction was heated for an additional two hours. The dimethylformamide was then removed in vacuo and the residue partitioned between ethyl acetate and saturated aqueous ammonium chloride. The aqueous layer was extracted with ethyl acetate, dried over magnesium sulfate and the solvent removed to provide a yellow oil (1.23 g). Purification by flash chromatography on silica gel (150 g) and eluting with 15% ethyl acetate, hexane yielded the product as a colorless oil (683 mg, 87%).

C. 2-Propyl-3-[2'-(2H-tetrazol-5-yl)[1,1'-biphenyl]-4-yl]oxy]-4-quinolinecarboxylic acid, 2-methyl-1-(1-oxopropoxy)propyl ester, monolithium salt The title B compound (680 mg, 1.27 mmol) was suspended in p-xylene (1.4 mL). Tributyltin azide (1.4 mL, 5.07 mmol) was added and the reaction was heated to 85° C. for 70 hours. The brown reaction mixture was cooled to room temperature and stirred with methanol for 30 minutes. The mixture was then adsorbed onto silica gel (2 g) and purified by flash chromatography on silica gel (125 g) eluted with acetic acid (5%), acetone (5%), toluene (90%) to provide a pale yellow solid (238 mg). This material was dissolved in a mixture of lithium carbonate (2 mL, 0.10M aq.), methanol (1 mL) and purified by column chromatography using HP-20 polystyrene resin (40 mL column volume) eluted with 100 mL each of water to 60% aqueous acetone in 5% increments. The product containing fractions were combined and lyophilized to yield the lithium salt as a white solid (100 mg, 14%). m.p. 145° C. to 165° C.

Elemental Analysis for $C_{33}H_{32}N_5O_5Li.2.3\ H_2O$
Calc'd: C 63.21; H 5.88; N 11.17;
Found: C 62.93; H 5.37; N 10.81.

EXAMPLE 6

2-Cyclopropyl-3-[[2'-(2H-tetrazol-5-yl)[1,1'-biphenyl]-4-yl]oxy]-4-quinolinecarboxylic acid, dilithium salt A. 2-Chloro-1-cycloproplylethanone A solution of ethereal diazomethane containing nom. 0.373 mol in ca. 700 mL (assume 73% yield from MNNG, Fieser & Fieser, "Reagents for organic Synthesis, Volume 1") was prepared as follows: To a rapidly stirred mixture of potassium hydroxide (210 mL, 40% aq.) and ether (700 mL) cooled in an ice bath was added portionwise 1-methyl-3-nitro-1-nitrosoguanidine (MNNG, 75 g, 0.510 mol). Diazomethane generation immediately gave rise to a bright yellow ether layer which was separated from the water by freezing the lower aqueous in a dry-ice/acetone cold bath. The ethereal diazomethane was decanted along with several rinses with ether into a 2 L flask cooled in an ice-bath. Cyclopropane carbonyl chloride (22 g, 0.210 mol) dissolved in ether (200 mL) was poured into the ether/diazomethane solution and the reaction kept at −20° C. overnight. The reaction mixture was next cooled in an ice-bath and gaseous hydrochloric acid was bubbled in until dissipation of the yellow color. The organic solution was transferred to a separatory funnel and rinsed with 1:1:1, water:brine:saturated sodium bicarbonate solution until the aqueous layer remained at pH 9, then with brine to neutral pH. The organic extract was dried (magnesium sulfate) and concentrated in vacuo to afford the title compound (23.55 g, 94%).

B. 4'-(2-Cyclopropyl-2-oxoethoxy)[1,1'-biphenyl]-2-carbonitrile

A mixture containing chloroketone (the title A compound; 9.6 g, 80.9 mmol), biphenyl nitrite (the title B compound of Example 1; 10.5 g, 53.1 mmol), potassium carbonate (11.4 g, 82.5 mmol), and KI (3.2 g, 19.2 mmol) in acetone (50 mL) was heated with stirring in a stoppered flask at 50° C. for five hours, then cooled to room temperature, diluted with ethyl acetate to a volume of 500 mL and filtered. The filtrate was rinsed with sodium bisulfite (300 mL, 5%), and brine, then dried (magnesium sulfate) and concentrated in vacuo to a gummy residue. The crude product was extracted into 400 mL of refluxing diisopropyl ether which was filtered hot and set aside to allow crystallization. A first crop provided 11.7 g of compound and a second another 0.42 g for a total recovery of 12.2 g (83%) of the title compound; m.p. 82–84° C.

Elemental Analysis for $C_{18}H_{15}NO_2$
Calc'd: C 77.96; H 5.45; N 5.05;
Found: C 77.60; H 5.35; N 4.74.

C. 1-Cyclopropyl-2-[[2'-(2H-tetrazol-5-yl)-[1,1'-biphenyl]-4-yl]oxy]ethanone

A mixture of nitrile (the title B compound; 11.1 g, 40 mmol) and tributyltin azide (40 g, 120 mmol) in xylenes (13 mL) was heated in a stoppered flask at 110° C. for 22 hours, then cooled to room temperature and stirred with methanol (100 mL) for one hour, then concentrated in vacuo. The residue was taken up in toluene (250 mL) and extracted with an excess of 1N aq. sodium hydroxide (ca. 170 mL) until TLC indicated that no product remained in the organic layer. The aqueous extract was stirred vigorously with ethyl acetate (500 mL) and acidified to pH 1–2 with 10% aq. hydrochloric acid. The organic phase was separated and the aqueous was extracted further with two 100 mL portions of ethyl acetate. The combined organic extract was rinsed with water and brine, then set aside at room temperature overnight. A total of 5.8 g of product the title compound (m.p. 190–191° C.) crystallized from the ethyl acetate solution. The mother liquor was then dried (sodium sulfate) and concentrated in vacuo to provide a second crop of 5.2 g (m.p. 188–190° C.). A third crop of 0.71 g (m.p. 184–185° C.) was also obtained to afford a total of 11.7 g of the title compound (91%). A sample recrystallized from acetonitrile had a melting point of 190° C. and the following microanalysis:

Elemental Analysis for $C_{18}H_{16}N_4O_2.0.05H_2O$
Calc'd: C 67.31; H 5.05; N 17.44;
Found: C 67.20; H 4.80; N 17.55.

D. 2-Cyclopropyl-3-[[2'-(2H-tetrazol-5-yl)-[1,1'-biphenyl]-4-yl]oxy]-4-quinolinecarboxylic acid Isatin (2.35 g, 16 mmol) was added to 30% aq. potassium hydroxide (41 mL) and the solution was stirred at room temperature for five minutes. Tetrazole ketone (the title C compound; 5.12 g, 16 mmol) was added and the mixture was stirred and heated in a 110° C. oil bath for three hours, then cooled to room temperature and acidified to pH 1–2 with 10% hydrochloric acid in the presence of ethyl acetate (200 mL). The organic layer was separated and the aqueous further extracted with ethyl acetate. The combined organic extract was rinsed with water and brine, then dried (magnesium sulfate), and concentrated in vacuo to yellow solid residue (7 g). Trituration with refluxing acetonitrile (200 mL) yielded the title compound (6.75 g, 93%); m.p. 239° C. (d).

Elemental Analysis for $C_{26}H_{19}N_5O_3.0.3H_2O$
Calc'd: C 69.28; H 4.32; N 15.91;
Found: C 69.19; H 4.25; N 16.06.

E. 2-Cyclopropyl-3-[[2'-(2H-tetrazol-5-yl)-[1,1'-biphenyl]-4-yl]oxy]-4-quinolinecarboxylic acid dilithium salt The title D compound (602 mg, 1.34 mmol) was neutralized with 1N aq. lithium hydroxide (2.95 mL) and purified on a 50 mL column of HP-20 which was eluted with a gradient from water to 5% acetone in water. Product containing fractions were pooled and lyophillized to afford the title compound (466 mg, 69%) the title compound as a 2.5 water hydrate (does not melt below 250° C.).

Elemental Analysis for $C_{26}H_{17}N_5O_3Li_2.2.5H_2O$
Calc'd: C 61.67; H 4.38; N 13.83;
Found: C 61.61; H 4.21; N 13.54.

EXAMPLE 7

2-Ethyl-3-[2'-(2H-tetrazol-5-yl)[1,1'-biphenyl]-4-yl]oxy]-4-quinolinecarboxylic acid, 2-methyl-1-(1-oxopropoxy)propyl ester, monopotassium salt A. 2-Ethyl-3-[2-[2-(triphenylmethyl)-2H-tetrazol-5-yl][1,1'-biphenyl]-4-yl]oxy]-4-quinolinecarboxylic acid To a mixture containing 278 mg (0.636 mmol) of the title compound of Example 2 and 186 mg (0.668 mmol) of triphenylmethyl chloride in 3.2 mL of acetone was added 97.5 microliters (0.699 mmol) of triethylamine. After two days the reaction mixture was diluted with methylene chloride and the resulting organic solution was washed with water. An emulsion resulted which required extraction with several portions of ethyl acetate. The combined organic extracts were dried with sodium sulfate and magnesium sulfate, and concentrated to a solid product. The aqueous solution was filtered to provide more solid product, then further extracted with toluene:methanol (10:1) to provide more product. The combined recovery of product was 436 mg.

B. 2-Ethyl-3-[2'-[2-(triphenylmethyl)-2H-tetrazol-5-yl][1,1'-biphenyl]-4-yloxy]-4-quinolinecarboxylic acid, 2-methyl-1-(1-oxopropoxy)propyl ester A mixture containing 0.636 mmol of the title A compound, 0.37 mL (2.22 mmol) of the title A compound of Example 5, 127 mg (0.763 mmol) of KI, 132 mg (0.954 mmol) of potassium carbonate, and 33.6 mg (0.127 mmol) of 18-crown-6 in 1.27 mL of dimethylformamide was heated at 90° C. for two hours, then cooled to room temperature and diluted with ethyl acetate and filtered. The organic solution was washed with aq. 5% sodium bisulfite and brine, dried over sodium sulfate and magnesium sulfate and concentrated. Chromatography on 25 grams of silica gel eluted with toluene:ether (40:1) gave the title compound (401 mg), characterized by proton and C-13 nmr and mass spectrum.

C. 2-Ethyl-3-[2'-(2H-tetrazol-5-yl)[1,1'-biphenyl]-4-yloxy)-4-quinolinecarboxylic acid, 2-methyl-1-(1-oxopropoxy) propyl ester, monopotassium salt To a solution of 401 mg (0.496 mmol) of the title B compound in a mixture of 9.9 mL of ethanol and 9.9 mL of tetrahydrofuran was added 9.9 mL of 2N aq. hydrochloric acid solution. The reaction was stirred for two hours and 15 minutes at room temperature, then neutralized to pH 7 with 20% aq. potassium bicarbonate. The resulting mixture was filtered through a nylon membrane and concentrated to remove most of the organic solvents. Chromatography on a 15 mL bed of HP-20 polystyrene resin using a water-acetone gradient elution gave, after lyophillization, 114 mg of the title compound which was characterized by proton and C-13 nmr, mass spectrum, and microanalysis. This material had a m.p. of 125–138° C.

Elemental Analysis for $C_{32}H_{30}N_5O_5K.1.135H_2O$
Calc'd: C 61.20; H 5.25; N 11.15;
Found: C 61.54; H 4.82; N 10.68.

EXAMPLE 8

7-Chloro-2-(cyclopropyl)-3-[[2'-(2H-tetrazol-5-yl)-[1,1'-biphenyl]-4-yl]oxy]-4-quinolinecarboxylic acid, dipotassium salt 6-Chloroisatin (A. E. Senear, H. Savgent, J. F. Mead, J. B. Koepfli, *J. Am. Chem. Soc.*, 6, 2695 (1946) (0.2 g, 1.1 mmol) and the title C compound of Example 6 (0.32 g, 1 mmol) were heated at 105° C. in 30% potassium hydroxide (4 mL) for two hours. The reaction mixture was acidified with 10% hydrochloric acid, extracted with ethyl acetate (2×, 150 mL), and the ethyl acetate extract was washed with brine, dried (sodium sulfate), and concentrated in vacuo. The resulting solid was redissolved in 1N potassium hydroxide (4 mL) and methanol (1 mL) and chromatogrtaphed through HP-20 (40 mL) using water (200 mL) followed by water (200 mL) containing 5% acetone. The appropriate fractions were combined and concentrated to give a white solid (0.33 g, 58%). m.p. >250° C.

Elemental Analysis for $C_{26}H_{16}N_5O_3ClK_2.0.77H_2O$
Calc'd: C 54.42; H 3.08; N 12.20; Cl 6.18;
Found: C 54.58; H 3.12; N 12.04; Cl 6.16.

EXAMPLE 9

2-Cyclopropyl-6-fluoro-3-[[2'-(2H-tetrazol-5-yl)-[1,1'-biphenyl]-4-yl]oxy]-4-quinolinecarboxylic acid, dipotassium salt 5-Fluoroisatin (0.19 g, 1 mmol) and the title C compound of Example 6 (0.32 g, 1 mmol) were heated at 105° C. in potassium hydroxide (4 mL, 30%) for four hours. The reaction mixture was acidified with 10% hydrochloric acid, extracted with ethyl acetate (2×, 200 mL), and the ethyl acetate extract was washed with water, brine, dried (sodium sulfate), and concetrated in vacuo. The residue was redissolved in 1N potassium hydroxide (4 mL) and methanol (0.5 mL) and chromatographed through HP20 (40 mL) using water (200 mL) followed by 5% acetone (200 mL) in water. The appropriate fractions were combined, stirred with charcoal (1 g) for one hour, filtered through celite and lyophilized to yield the title compound (0.28 g, 60%). m.p. >250° C.

Elemental Analysis for $C_{26}H_{16}N_5O_3FK_2.1.8H_2O$
Calc'd: C 54.20; H 3.43; N 12.16; F 3.30;
Found: C 54.16; H 3.33; N 12.20; F 3.31.

EXAMPLE 10

2-Cyclopropyl-8 methyl-3-[[2'-(2H-tetrazol-5-yl)-[1,1'-biphenyl]-4-yl]oxy]-4-quinolinecarboxylic acid, dipotassium salt A. 2,3-Dihydro-7-methyl-1H-indole-2,3-dione Oxalyl chloride (5.8 g, 46 mmol) in tetrahydrofuran (2 mL) was heated to reflux and o-toluidine hydrochloride was added portionwise over ten minutes. After addition, the reaction mixture was refluxed for four hours and concentrated in vacuo to yield 1-Chloro-2-[(2-methylphenyl)amino]ethandione. This intermediate was dissolved in chloroform (4 mL) and aluminum chloride (2.6 g) was added portionwise. The reaction mixture was heated at reflux overnight, and chromatographed through Merck silica gel (100 g) using (9:1:0.1) toluene:acetone:acetic acid solvent system. The appropriate fractions were combined and concentrated to yield the title compound (90 mg, 5.6%).

B. 2-Cyclopropyl-6-fluoro-3-[(2'-(2H-tetrazol-5-yl)[1,1'-biphenyl]-4-yl]oxy]-4-quinolinecarboxylic acid, dipotassium salt The above isatin (the title A compound; 88 mg, 0.55 mmol) and the title C compound of Example 6 were combined in potassium hydroxide (2 mL, 30%) and heated at 105° C. for six hours. The reaction mixture was acidified with 6N hydrochloric acid and extracted with ethyl acetate (3×, 80 mL). The extracts were washed tetrahydrofuran with brine, dried (sodium sulfate), concentrated and the residue was chromatographed (2×) through Merck silica gel (50 g). The appropriate fractions were combined and concentrated to give the title compound contaminated with a small amount of an unknown by-product. This residue was dissolved in 1N potassium hydroxide (0.5 mL) and chromatographed through HP-20 using water (100 mL) followed by 5% acetone (200 mL) in water. The appropriate fractions were combined, concentrated to 30 mL, filtered through milliopore and lyophilized to yield the title compound (70 mg, 24.3%). m.p. >250° C.

Elemental Analysis for $C_{27}H_{19}N_5O_3K_2.2.14H_2O$
Calc'd: C 56.09; H 4.06; N 12.11;
Found: C 56.50; H 3.74; N 11.70.

EXAMPLE 11

2-Cyclopropyl-3-[[2'-(2H-tetrazol-5-yl)[1,1'-biphenyl]-4-yl]oxy]-4,5-quinolinedicarboxylic acid, tripotassium salt A. 3,3-Dibromo-2,3-dihydro-2-oxo-1H-indole-4-carboxylic acid, methyl ester 2,3-Dihydro-2-oxo-1H-indole-4-carboxylic acid, methyl ester, (C. A. Grob and 0. Weissbach, *Hely. Chim. Acta,* vol. 44, p. 1736, 1961) (2 g, 11.4 mmol) was dissolved in t-butylhydroxide (120 mL) containing 0.5 mL of water. Pyridine.hydrogen bromide.bromine (14.6 g, 45.7 mmol) was added and the mixture was stirred at room temperature for 16 hours. The reaction was quenched by the addition of water and the t-butylhydroxide was distilled off. The resulting residue was partitioned between water and ethyl acetate, and the ethyl acetate was dried with magnesium sulfate, filtered and concentrated in vacuo to yield the title compound (3.92 g, 98%).

B. 2,3-Dihydro-2,3-dioxo-1H-indole-4-carboxylic acid, methyl ester

The title A compound (3.49 g, 10 mmol) in acetonitrile (150 mL) and water (10 mL) was stirred with silver trifluoroacetate (4.5 g, 20 mmol) at 80° C. for one hour and 30 minutes. The reaction mixture was concentrated in vacuo and chromatographed through Merck silica gel (180 g) using a 3:7 acetone:hexane solvent system. The appropriate fractions were combined and concentrated to yield the title compound as a orange-brown solid.

C. 2-Cyclopropyl-3-[[2'-(2H-tetrazol-5-yl)-[1,1'-biphenyl]-4-yl]oxy]-4,5-quinolinedicarboxylic acid, tripotassium salt The title B compound (0.1 g, 0.49 mmol) and the title C compound of Example 6 (0.156 g, 0.49 mmol) were heated at 108° C. in 30% potassium hydroxide (3 mL) overnight. 1N Hydrochloric acid (2 mL) was added to the reaction and product was extracted with ethyl acetate (4×, 50 mL). The ethyl acetate extracts were washed with brine, dried (sodium sulfate), and concentrated in vacuo. The resulting residue was chromatographed twice through Merck silica gel (50 g) with acetone containing 1% of acetic acid. The appropriate fractions were combined, concentrated and the residue was dissolved in 1N potassium hydroxide (0.9 mL). This was passed twice through HP20 (20 mL) using water. The appropriate fractions were combined and concentrated to yield the title compound (60 mg, 25%). m.p. >250° C.

Elemental Analysis for $C_{27}H_{16}N_5O_5K_3 \cdot 2.8H_2O$
Calc'd: C 49.27; H 3.31; N 10.64;
Found: C 49.62; H 3.03; N 10.28.

EXAMPLE 12

2-Propyl-3-[[2'-(1H-tetrazol-5-yl)[1,1'-biphenyl]-4-yl]oxy]-4-quinolinecarboxylic acid, butyl ester, monopotassium salt A. 3-[[2'-Cyano[1,1'-biphenyl]-4-yl]oxy]-2-propyl-4-quinolinecarboxylic acid, butyl ester A solution of the title E compound of Example 1 (0.50 g, 1.22 mmol) and n-butyl iodide (0.27 mL, 2.45 mmol) in dry dimethylformamide (2.7 mL, room temperature, argon) with cesium carbonate (1.19 g, 3.67 mmol) was stirred for six hours and 30 minutes. The reaction was quenched by the rapid addition of 0.25M potassium bisulfate (30 mL) solution and ethyl acetate (25 mL). After separation of the layers, the aqueous layer was washed once with ethyl acetate (25 mL), the combined ethyl acetate layers were washed three times with 0.25M potassium bisulfate solution (15 mL each), brine, dried over sodium sulfate, and concentrated to yield a viscous oil (0.55 g). Flash chromatography on silica gel (33 g), eluting with 2 L of 95:5 hexanes:ethyl acetate, yielded the title compound as a viscous yellow oil (0.39 g, 69%).

B. 2-Propyl-3-[[2'-(1H-tetrazol-5-yl)-[1,1'-biphenyl]-4-yl]oxy]-4-quinolinecarboxylic acid, butyl ester A solution of the title A compound (0.39 g, 0.84 mmol) and tri-n-butyltin azide (0.76 g, 2.30 mmol) in o-xylene (0.40 mL) was heated to 108° C. for 79 hours. After cooling to room temperature, methanol (20 mL) was added and the solution was stirred for 20 minutes. The methanol was removed under vacuum, the residue was dissolved in ethyl acetate (20 mL), washed with 1.0M trisodium citrate solution (3×), brine, dried over sodium sulfate, and concentrated to yield a dark tan oil (1.40 g). Flash chromatography on silica gel (84 g), eluting with 1 L of 7:3 hexanes:ethyl acetate, 1.2 L of 7:2.9:0.1 Hexanes:ethyl acetate: acetic acid yielded the title compound as a light yellow glass (0.35 g, 82%).

C. 2-Propyl-3-[[2'-(1H-tetrazol-5-yl)[1,1'-biphenyl]-4-yl]oxy]-4-quinolinecarboxylic acid, butyl ester, monopotassium salt A solution of the title B compound (0.35 g, 0.69 mmol) in tetrahydrofuran (2.4 mL) was treated with a solution of potassium bicarbonate (82.8 mg, 0.83 mmol) in water (1.8 mL). The cloudy solution was stirred for 45 minutes. Tetrahydrofuran was removed under vacuum and the residue was desalted and purified through a column of HP-20 reverse-phase resin (15 mL wet volume), eluting with water (60 mL) and 9:1 water:acetonitrile (50 mL) to yield, after lyophilization, the title compound as a white solid (0.27 g, 70%); m.p. 98–116.5° C. with foaming.

Elemental Analysis for $C_{30}H_{28}N_5O_3K \cdot 0.73H_2O$
Calc'd: C 64.47; H 5.31; N 12.53;
Found: C 64.47; H 5.22; N 12.45.

EXAMPLE 13

2-Propyl-3-[[2'-(1H-tetrazol-5-yl)[1,1'-biphenyl]-4-yl]oxy]-4-quinolinecarboxylic acid, 2-(1,1 -dimethylethoxy)-2-oxoethyl ester, monopotassium salt A. 3-[[2'-Cyano[1,1'-biphenyl]-4-yl]oxy]-2-propyl-4-quinolinecarboxylic acid, 2-(1,1-dimethyl-ethoxy)-2-oxoethyl ester A solution of the title E compound of Example 1 (0.50 g, 1.2 mmol) in dimethylformamide (2.7 mL, room temperature, argon) with cesium carbonate (1.19 g, 3.7 mmol) was treated with t-Butyl bromoacetate (0.40 mL, 2.45 mmol). The pink reaction mixture was stirred for six hours. The reaction was quenched by the rapid addition of 0.25M potassium bisulfate solution (30 mL) and ethyl acetate (25 mL). After separation of the layers, the aqueous layer was washed once with ethyl acetate (25 mL), the combined ethyl acetate layers were washed three times with 0.25M potassium bisulfate solution (15 mL each), brine, dried over sodium sulfate, and concentrated to yield a dark red oil (0.84 g). Flash chromatography on silica gel (38 g), eluting with 1 L of 98:2, 1 L of 96:4, and 1 L of 85:15 hexanes:ethyl acetate yielded 0.40 g (63%) the title compound.

B. 2-Propyl-3-[[2'-(1H-tetrazol-5-yl)[1,1'-biphenyl]-4-yl]oxy]-4-quinolinecarboxylic acid, 2-(1,1-dimethylethoxy)-2-oxoethyl ester A solution of the title A compound (0.40 g, 0.77 mmol) in tri-n-butyltin azide (0.76 g, 2.3 mmol) and o-xylene (0.40 mL) was heated in a sealed flask (initially purged with argon) at 108° C. for 79 hours. After cooling to room temperature, methanol (20 mL) was added and the solution was stirred for 20 minutes. After removal of the methanol under vacuum, the residue was dissolved in ethyl acetate (20 mL), washed with 1.0M trisodium citrate solution three times, brine, dried over sodium sulfate, and concentrated to yield a light tan oil (1.15 g). Flash chromatography on silica gel (69 g), eluting with 90:10 hexanes:ethyl acetate, 70:30 hexanes:ethyl acetate, and 70:29:1 hexanes:ethyl acetate:acetic acid yielded the title compound (0.32 g, 73%); m.p. 70.5–135.0° C. with foaming.

C. 2-Propyl-3-[[2'-(1H-tetrazol-5-yl)[1,1'-biphenyl]-4-yl]oxy]-4-quinolinecarboxylic acid, 2-(1,1-dimethylethoxy)-2-oxoethyl ester, monopotassium salt A solution of the title B compound (0.32 g, 0.57 mmol) in tetrahydrofuran (2.0 mL)/water (1.5 mL, room temperature, argon) was treated with a solution of potassium bicarbonate (68.1 mg, 0.68 mmol) in water (1.5 mL). The slightly cloudy reaction solution was stirred for 30 minutes. Tetrahydrofuran was removed under vacuum and the cloudy aqueous solution was purified and de-salted through a column of HP-20 reverse-phase resin (20 mL wet volume), eluting with water containing increasing proportions of methanol to yield, after methanol removal (under vacuum) followed by lyophilization, the title compound as a white solid (0.14 g, 41%); m.p. 130–145° C. with foaming.

Elemental Analysis for $C_{32}H_{30}N_5O_5K \cdot 1.79\ H_2O$
Calcd: C 60.44; H 5.32; N 11.01;
Found: C 60.69; H 5.07; N 10.76.

EXAMPLE 14

2-Ethyl-3-[[2'-(2H-tetrazol-5-yl)[1,1'-biphenyl]-4-yl]oxy]-4-quinolinecarboxylic acid, 2-(1,1-dimethylethoxy)-2-oxoethyl ester, monopotassium salt A. 3-[(2'-Cyano[1,1'-biphenyl]-4-yl)oxy]-2-ethyl-4-quinolinecarboxylic acid, 2-(1,1-dimethylethoxy)-2-oxoethyl ester A mixture of the title C compound of Example 2 (500 mg, 1.27 mmol), tert-butyl bromoacetate (0.41 mL, 2.5 mmol), and cesium carbonate (975 mg, 3.0 mmol) in dimethylformamide (5 mL) was stirred at 25° C. for 18 hours. The mixture was then poured into brine, extracted with ethyl acetate, dried (magnesium sulfate), and concentrated in vacuo. The residue was purified by flash chromatography on silica gel (315 g), eluting with 3:1 hexane:ethyl acetate. Fractions containing the major product were combined and concentrated, and the residue was triturated with hexane/ether to give the title compound as a white solid (440 mg, 70%); m.p. 83–85° C.

B. 2-Ethyl-3-[[2'-(1H-tetrazol-5-yl)[1,1'-biphenyl]-4-yl]oxy]-4-quinolinecarboxylic acid, 2-(1,1-dimethylethoxy)-2-oxoethyl ester, monopotassium salt A mixture of the title A compound (400 mg, 0.80 mmol) and tributyltin azide (800 mg, 2.4 mmol) in o-xylene (0.8 mL) was stirred at 100° C. for 20 hours, after which it was chromatographed directly on a silica gel column (65 g, sorbsil). Fractions were eluted with 6:4:1 hexane:ethyl acetate:acetic acid; those containing the major UV absorbing component were combined and concentrated. The residue was dissolved in methanol (5 mL) and diluted with 0.1N potassium carbonate solution (5 mL). The resulting solution was applied to a column of macroreticullar polystyrene (J-Gel, 30×, 500 mm), and was eluted first with water (1,000 mL), then with a linear gradient from 0 to 100% aqueous methanol over 15 minutes (50 mL/minute). Fractions containing the major UV absorbing component were combined, concentrated, and lyophilized to give the title compound as a white solid (125 mg, 25%); m.p. 152–8° C.

Elemental Analysis for $C_{31}H_{28}N_5O_5K \cdot 0.73\ H_2O$
Calcd: C 61.77; H 4.93; N 11.62;
Found: C 61.77; H 4.76; N 11.44.

EXAMPLE 15

2-Ethyl-3-[[2'-(1H-tetrazol-5-yl)[1,1'-biphenyl]-4-yl]oxy]-4-quinolinecarboxylic acid, butyl ester monopotassium salt A. 3-[(21-Cyano[1,1'-biphenyl]-4-yl)oxy]-2-ethyl-4-quinolinecarboxylic acid, butyl ester A mixture of the title C compound of Example 1 (500 mg, 1.27 mmol), n-butyliodide (0.28 mL, 2.5 mmol), and cesium carbonate (975 mg, 3.0 mmol) in dimethylformamide (5 mL) was stirred at 25° C. for 20 hours. The mixture was then poured into brine, extracted with ethyl acetate, dried (magnesium sulfate), and concentrated in vacuo. The residue was purified by flash chromatography on silica gel (300 g), eluting with 3:1 hexane:ethyl acetate. Fractions containing the major product were combined and concentrated to give the title compound as an oil (425 mg, 74%).

B. 2-Ethyl-3-[[2'-(1H-tetrazol-5-yl)[1,1'-biphenyl]-4-yl]oxy]-4-quinolinecarboxylic acid, butyl ester, monopotassium salt A mixture of the title A compound (400 mg, 0.89 mmol) and tributyltinazide (1.0 g, 3.0 mmol) in o-xylene (0.8 mL) was stirred at 90° C. for 72 hours, after which it was chromatographed directly on a silica gel column (65 g, sorbsil). Fractions were eluted with 15:10:1 hexane:ethyl acetate: acetic acid; those containing the major UV absorbing component were combined and concentrated. The residue was rechromatographed, eluting with 20:1 ethyl acetate: (pyridine 20:acetic acid 6: water 11), to give an oil. The oil was dissolved in methanol (10 mL) and diluted with 0.1N potassium carbonate solution (7 mL). The resulting solution was applied to a column of macroreticullar polystyrene (J-Gel, 30×, 500 mm), and was eluted first with 1,000 mL of water then with a linear gradient from 0 to 100% aqueous methanol over 15 minutes (50 mL/minute). Fractions containing the major UV absorbing component were combined, concentrated, and lyophilized to give the title compound as a white solid (190 mg, 40%). m.p. 204–208° C.

Elemental Analysis for $C_{29}H_{26}N_5O_3K \cdot 0.36H_2O$
Calc'd: C 64.73; H 4.93; N 13.01;
Found: C 65.11; H 5.10; N 12.56.

EXAMPLE 16

2-Ethyl-3-[[2'-(1H-tetrazol-5-yl)[1,1'-biphenyl]-4-yl]oxy]-4-quinolinecarboxylic acid, 1-(2,2-dimethyl-1-oxopropoxy)-2-methylpropyl ester, monopotassium salt A. 2-Ethyl-3-[[2'-[2-(triphenylmethyl)-2H-tetrazol-5-yl][1,1'-biphenyl]-4-yl]oxy]-4-quinolinecarboxylic acid A mixture of the title compound of Example 2, 2-ethyl-3-[[2'-(2H-tetrazol-5-yl)[1,1'-biphenyl]-4-yl]-oxy]-4-quinolinecarboxylic acid, dilithium salt (700 mg, 1.6 mmol), triethyl amine (245 microliters, 1.76 mmol), triphenylmethyl chloride (468 mg, 1.68 mmol) and acetone (8 mL) was stirred at room temperature for 36 hours. The mixture was concentrated in vacuo to yield the crude product as a waxy solid (1.35 g, 100%).

B. 2,2-Dimethylpropanoic acid, 1-chloro-2-methylpropyl ester

To freshly fused zinc chloride (70 mg) and trimethylacetylchloride (12.3 mL, 100 mmol) cooled in an ice bath in dichloromethane (25 mL) was added isobutyraldehyde (9.08 mL, 100 mmol), keeping the reaction temperature <25° C. The solution was allowed to warm to room temperature and stirred one hour, washed with a solution of sodium acetate (50 mL, 20%), dried (magnesium sulfate), and concentrated under low vacuum to remove dichloromethane (yield 16.18 g, 84 mmol, 84%).

C. 2-Ethyl-3-[[2'-[2-(triphenylmethyl)-1H-tetrazol-5-yl][1,1'-biphenyl]-4-yl]oxy]-4-quinolinecarboxylic acid, 1-(2,2-dimethyl-1-oxopropoxy)-2-methylpropyl ester A mixture of the title A compound (1.215 g, 1.44 mmol, at assumed 90% purity), potassium iodide (287 mg, 1.73 mmol), potassium carbonate (398 mg, 2.88 mmol), 18-crown-6 (76 mg, 0.29 mmol), dimethylformamide (2.88 mL), and the title B compound (972 mg, 5.04 mmol) were combined and stirred at 90° C. under argon for four hours. The mixture was cooled to room temperature, poured into ethyl acetate (200 mL), washed with water (150 mL), sodium bisulfite (150 mL, 20% aq.), and brine (150 mL), dried (magnesium sulfate), and concentrated to a crude oil in vacuo. The crude product was purified using flash chromatography (65 g EM silica, eluted with hexane:ethyl acetate 6:1), and the major product fractions were pooled and concentrated in vacuo to yield the title compound as a light brown semi-solid (990 mg, 1.18 mmol, 74%).

D. 2-Ethyl-3-[[2-(1H-tetrazol-5-yl)[1,1'-biphenyl]-4-yl]oxy]-4-quinolinecarboxylic acid, 1-(2,2-dimethyl-1-oxopropoxy)-2-methylpropyl ester, monopotassium salt The title C compound (870 mg, 1.04 mmol) was dissolved and stirred in a solution of 20.8 mL each of ethanol, tetrahydrofuran, and 2N hydrochloric acid for two hours. The solution was concentrated to approximately 30 mL, and a white, waxy, flaky solid formed and was removed by filtration. The remaining solution was adjusted to pH 7.4 with potassium bicarbonate (20% aq.) and purified using preprative HPLC (Jordi-gel polystyrene column eluting with a 30 minute water to methanol linear gradient). Analytical HPLC and NMR revealed that the product was contaminated with triphenyl carbinol, and additional purification using flash chromatography (60 g silica eluted with hexane:ethyl acetate:acetic acid 8:4:0.1) was performed. The product was then dissolved in ethanol/water and readjusted to pH 7.4 with potassium bicarbonate (20% aq.) and purified using preprative HPLC (Jordi-gel polystyrene column eluting with a 30 minute water to methanol linear gradient). The final product was obtained by lyophilization from water (20 mL) and ethanol (2 mL) to provide the title compound as a white solid (330 mg, 0.53 mmol, 51%); m.p. 184–190° C.

Elemental Analysis for $C_{34}H_{34}N_5O_5K \cdot 1.0H_2O$
Calc'd: C 62.85; H 5.58; N 10.78; K 6.02;
Found: C 62.64; H 5.55; N 10.78; K 5.73.

EXAMPLE 17

2-Cyclopropyl-3-[[2'-[2-[1-(2,2-dimethyl-1-oxopropoxy)-2-methylpropyl]-2H-tetrazol-5-yl][1,1'-biphenyl]-4-yl]oxy]-4-quinolinecarboxylic acid A. 2-Cyclopropyl-3-[[2'-[2-(triphenylmethyl)-2H-tetrazol-5-yl][1,1'-biphenyl]-4-yl]oxy]-4-quinolinecarboxylic acid The title D compound of Example 6 (800 mg, 1.77 mmol, 1 eq.) was dissolved in methylene chloride (8.9 mL, 0.2M), and triethylamine (0.62 mL, 4.43 mmol, 2.5 eq.), dimethylaminopyridine (22 mg, 0.177 mmol, 0.1 eq.) and chloro triphenylmethane (597 mg, 2.14 mmol, 1.2 eq.) were added. The reaction was stirred at room temperature for four hours, diluted with ethyl acetate, washed with ammonium chloride/water and saturated sodium chloride. The organic liquid was dried (magnesium sulfate) and concentrated to give the title compound.

B. 2-Cyclopropyl-3-[[2'-[2-(triphenylmethyl)-2H-tetrazol-5-yl][1,1'-biphenyl]-4-yl]oxy]-4-quinolinecarboxylic acid, 2-propenyl ester The title A compound was dissolved in dimethylformamide (5.9 mL, 0.3M), and allyl bromide (1.28 g, 10.62 mmol, 6 eq.) and potassium carbonate (612 mg, 4.43 mmol, 2.5 eq.) were added. The reaction was stirred at room temperature for 15 hours and then at 50° C. for two hours. The reaction mixture was diluted with ethyl acetate, washed with ammonium chloride/water and sat. sodium chloride. The organic liquid was dried (magnesium sulfate), filtered and concentrated to afford the title compound.

C. 2-Cyclopropyl-3-[[2'-(2H-tetrazol-5-yl)-[1,1'-biphenyl]-4-yl]oxy]-4-quinolinecarboxylic acid 2-prolpenyl ester The title B compound was dissolved in ethanol (18 mL) and tetrahydrofuran (18 mL), and hydrochloric acid (2N, 18 mL) was added. The reaction was stirred at room temperature for three hours, and extracted with ethyl acetate. The extracts were dried (magnesium sulfate) and concentrated. The residue was chromatographed on silica gel eluting with methylene chloride:methanol (100:0.3) and then methylene chloride:methanol (100:2~6) to afford the title compound (550 mg, 64%).

D. 2-Cyclopropyl-3-[[2'-[2-[1-(2,2-dimethyl-1-oxopropoxy)-2-methylpropyl]-2H-tetrazol-5-yl][1,1'-biphenyl]-4-yl]oxy]-4-quinolinecarboxylic acid, 2propenyl ester A mixture of the title C compound (550 mg, 1.12 mmol, 1 eq.), the title B compound of Example 16; 2,2-dimethylpropanoic acid, 1-chloro-2-methylpropyl ester (1.30 g, 6.74 mmol, 6 eq.), activated molecular sieves (4A, 1.1 g, 200% by wt.), silver oxide (1.04 g, 4.50 mmol, 4.4 eq.) and tetrahydrofuran (5.6 mL, 0.2M) was heated at 65° C. for 18 hours. The reaction mixture was shaken with ethyl acetate and ammonium chloride/water. The organic layer was washed with brine, dried (magnesium sulfate), filtered and concentrated. The residue was chromatographed on a preparative silica gel plate developing with hexane:ethyl acetate (2:1) to give the title compound (345 mg, 48%).

E. 2-Cyclopropyl-3-[[2'-[2-[1-(2,2-dimethyl-1-oxopropoxy)-2-methylpropyl]-2H-tetrazol-5-yl][1,1'-biphenyl]-4-yl]oxy]-4-quinolinecarboxylic acid The title D compound (320 mg, 0.50 mmol, 1 eq.) was dissolved in tetrahydrofuran (3.8 mL, 0.13M), and dimedone (209 mg, 1.49 mmol, 3 eq.) and Pd(triphenylphosphine)4 were added. The mixture was stirred at room temperature for 30 minutes and then concentrated. The residue was chromatographed on silica gel eluting with methylene chloride containing increasing proportions of methanol to afford the title compound (280 mg, 93%), m.p. 165–168° C.

Elemental Analysis for $C_{35}H_{35}N_5O_5 \cdot 1.5H_2O$
Calcd: C 66.44; H 6.05; N 11.07;
Found: C 66.24; H 5.64; N 10.65.

EXAMPLE 18

2-Cyclopropyl-3-[[2'-(2H-tetrazol-5-yl)[1,1'-biphenyl]-4-yl]oxy]-4-quinolinecarboxylic acid, (5-methyl-2-oxo-1,3-dioxol-4-yl)methyl ester, monopotassium salt A. 4,5-Dimethyl-1,3-dioxole-2-one To 3-hydroxy-2-butanone (17.62 g, 0.2 mol, 1.0 eq.) and N,N-dimethylaniline (25.4 g, 0.21 mol, 1.05 eq.) in methylene chloride (200 mL) at 0° C., a solution of phosgene in toluene (1.93M, 109 mL, 0.21 mol, 1.05 eq.) was added. The reaction was stirred at 0° C. for 15 minutes and then at room temperature for four days. Solvents of the reaction were distilled out until the bath temperature reached 1600C. The mixture was cooled to room temperature, diluted with ether, washed with 1N hydrochloric acid and saturated sodium chloride. The organic liquid was dried (magnesium sulfate) and concentrated. The residue was recrystallized (ether/hexane) to afford the title compound as a white solid (12.64 g, 55%).

B. 4-(Bromomethyl)-5-methyl-1,3-dioxole-2-one

To a solution of the title A compound (12.46 g, 0.111 mol, 1.0 eq.) in carbon tetrachloride (554 mL, 0.2M), N-bromosuccinimide (19.72 g, 0.111 mol, 1 eq.) and azobisisobutyronitrile (253 mg) were added. The reaction was heated at reflux for 30 minutes. The mixture was cooled to room temperature and concentrated to half volume, and filtered. The solvent of the filtrate was removed and the residue was distilled under vacuum to afford the title compound; b.p. 124° C./10 mmHg (14 g, 65%).

C. 2-Cyclopropyl-3-[[2'-[2-(triphenylmethyl)-2H-tetrazol-5-yl][1,1'-biphenyl]-4-yl]oxy]-4-quinolinecarboxylic acid, (5-methyl-2-oxo-1,3-dioxol-4-yl)methyl ester To the title A compound of Example 17, 2-cyclopropyl-3-[[2'-[2-(triphenylmethyl)-2H-tetrazol-5-yl][1,1'-biphenyl]-4-yl]oxy]-4-quinolinecarboxylic acid (1.32 g, 1.91 mmol, 1 eq.), and the title B compound (1.84 g, 9.54 mmol, 5 eq.) in dimethylformamide (3.8 mL, 0.5M), potassium carbonate (0.66 g, 4.77 mmol, 2.5 eq.) was added. The mixture was stirred at room temperature for 21 hours, diluted with ethyl acetate and filtered. The filtrate was washed with ammonium chloride/water and saturated sodium chloride, dried (magnesium sulfate), filtered and concentrated to afford the title compound.

D. 2-Cyclopropyl-3-[[2'-(2H-tetrazol-5-yl)-[1,1'-biphenyl]-4-yl]oxy]-4-quinolinecarboxylic acid, (5-methyl-2-oxo-1,3-dioxol-4-yl)methyl ester The title C compound was dissolved in ethanol (20 mL) and tetrahydrofuran (20 mL), and hydrochloric acid (2N, 20 mL) was added. The mixture was stirred at room temperature for one hour, and extracted with methylene chloride. The organic extracts were concentrated and the residue was chromatographed on silica gel eluting with methylene containing increasing proportions of methanol to give the title compound (631 mg, 59%).

E. 2-Cyclopropyl-3-[[2'-(2H-tetrazol-5-yl)-[1,1'-biphenyl]-4-yl]oxy]-4-quinolincarboxylic acid, (5-methyl-2-oxo-1,3-dioxol-4-yl)methyl ester, monopotassium salt To a solution of the title D compound (631 mg, 1.12 mmol, 1 eq.) in methanol (40 mL) at 0° C., a solution of potassium bicarbonate (124 mg, 1.24 mmol, 1.1 eq.) in water (10 mL) was added. The mixture was stirred at room temperature for 20 minutes. Most solvents of the reaction were evaporated under vacuum. The residue was chromatographed on an HP-20 column eluting with water containing increasing proportions of acetone to give the title compound (230 mg, 47%); m.p. 124–127° C.

Elemental Analysis for $C_{31}H_{22}N_5O_6K$
Calc'd: C 62.09; H 3.70; N 11.68;
Found: C 63.78; H 4.38; N 11.21.

EXAMPLE 19

2-Cyclopropyl-3-[[2'-(2H-tetrazol-5-yl)[1,1'-biphenyl]-4-yl]oxy]-4-quinolinecarboxylic acid, (5-methyl-2-oxo-1,3-dioxol-4-yl)methyl ester To a solution of the title D compound of Example 18, 2-cyclopropyl-3-[[2'-(2H-tetrazol-5-yl)[1,1'-biphenyl]-4-yl]oxy]-4-quinolinecarboxylic acid, (5-methyl-2-oxo-1,3-dioxol-4-yl)methyl ester, monopotassium salt (631 mg, 1.12 mmol, 1 eq.) in methanol (40 mL) at 0° C., a solution of potassium bicarbonate (124 mg, 1.24 mmol, 1.1 eq.) in water (10 mL) was added. The mixture was stirred at room temperature for 20 minutes. Most solvents of the reaction were evaporated under vacuum. The residue was chromatographed on an HP-20 column eluting with water, water:acetone (100:3~15), and followed by water:acetone (100:25~30) to give the title compound of Example 18, 2-Cyclopropyl-3-[[2'-(2H-tetrazol-5-yl)[1,1'-biphenyl]-4-yl]oxy]-4-quinolinecarboxylic acid, (5-methyl-2-oxo-1,3-dioxol-4-yl)methyl ester, monopotassium salt (230 mg, 34%). The HP-20 column was then eluted with methanol to afford the title compound (starting material, 170 mg, 27%). m.p. 103–106° C.

Elemental Analysis for $C_{31}H_{23}N_5O_6 \cdot 0.4H_2O$
Calc'd: C 65.47; H 4.22; N 12.31;
Found: C 65.72; H 3.93; N 12.15.

EXAMPLE 20

6-Bromo-2-propyl-3-[[2'-(2H-tetrazol-5-yl)[1,1'-biphenyl]-4-yl]oxy]-4-quinolinecarboxylic acid, dipotassium salt A. 3-[[2'-(Aminocarbonyl)[1,1'-biphenyl]-4-yl]oxy]-6-bromo-2-propyl-4-quinolinecarboxylic acid A mixture of 5-bromo isatin (1 g, 4.42 mmol) and the title C compound of Example 1, 4'-(2-oxopentyloxy)-[1,1'-biphenyl]-2-carbonitrile (1.23 g, 4.41 mmol) in potassium hydroxide (11 mL, 30% aq.) was heated in a 105° C. oil bath for six hours. The reaction mixture was next cooled to room temperature and acidified and extracted with ethyl acetate. The organic extract was rinsed with brine, dried (magnesium sulfate) and evaporated to give ca. 2.5 g of crude product. Trituration with ethyl acetate-hexanes yielded 1.97 g of crude product (88%) which was carried on to the next reaction.

B. 6-Bromo-3-[(2'-cyano[1,1'-biphenyl]-4-yl)oxy]-2-propyl-4-quinolinecarboxylic acid A solution of the title A compound (1.87 g, 3.70 mmol) in a mixture of dioxane (7.5 mL) and pyridine (3.74 mL) was cooled to 0° C. and treated with trifluoroacetic anhydride (2.78 g, 1.87 mL, 13.2 mmol). The cold bath was removed and the reaction was stirred at ambient temperature overnight, then poured into hydrochloric acid (80 mL, 1N aq.) and extracted with ethyl acetate (110 mL). The organic extract was rinsed with three 40 mL portions of water, brine, and dried (magnesium sulfate). Concentration in vacuo gave a crude product (3 g). Trituration with hot ethyl acetate-hexanes gave the title compound (1.04 g). The mother liquor was concentrated and flash chromatographed on silica gel (133 g) eluted with 7:4:0.1, hexanes:ethyl acetate:acetic acid to yield further product (222 mg). Total yield was 1.26 g (70%).

C. 6-Bromo-2-propyl-3-[[2'-(2H-tetrazol-5-yl)[1,1'-biphenyl]-4-yl]oxy]-4-quinolinecarboxylic acid, dipotassium salt A mixture of the title B compound (222 mg, 0.456 mmol), $(nBu)_3Sn—N_3$ (605 mg, 1.82 mmol) and xylenes (1 mL) was heated at 100° C. in a stoppered flask for 16 hours. Additional $(nBu)_3Sn—N_3$ (480 mg) was added and heating at 100° C. was continued for another 19 hours. Overnight heating was repeated twice again, each time with an additional 300 mg of $(nBu)_3Sn—N_3$. With disapppearance of starting material judged to be essentially complete, the cooled reaction was treated with methanol (3 mL), stirred for 30 minutes, concentrated in vacuo, redissolved in methylene chloride (0.5 mL) and flash chromatographed on silica gel (25 g) eluted with 30:1:0.5, methylene chloride:methanol:acetic acid. Pooled product fractions gave desired acid tetrazole (190 mg). This material was converted to its desired dipotassium salt by treatment with potassium hydroxide (0.86 mL, 1N aq.) and purified on a 20 mL column of HP-20 which was eluted with a gradient from 5% to 10% aqueous acetone. Product containing fractions were pooled and lyophillized to afford the title compound (150 mg, 51%) as a 2.39 water hydrate (does not melt below 250° C.).

Elemental Analysis for $C_{26}H_{18}N_5O_3BrK_2 \cdot 2.39H_2O$
Calc'd: C 48.07; H 3.53; N 10.78; Br 12.30
Found: C 48.07; H 3.34; N 10.56; Br 12.54.

EXAMPLE 21

2-Propyl-3-[[2'-(2H-tetrazol-5-yl)[1,1'-biphenyl]-4-yl]oxy]-4-quinolinecarboxylic acid, 1-oxide, dilithium salt The title compound of Example 1, 2-propyl-3-([2'-(2H-tetrazol-5-yl)[1,1'-biphenyl]-4-yl]oxy]-4- quinolinecarboxylic acid, dilithium salt (51 mg, 0.11 mmol) was dissolved in approximately 5 mL of water and 80% monoperoxyphthalic acid, magnesium salt (MMPP) (516 mg, 0.25 mmol) was added and the reaction was heated to 50° C. for two hours. Another 345 mg of MMPP was added to the reaction over the course of three hours at 50° C. The reaction was then cooled to room temperature and the pH of the solution was made acidic by the addition of 1N hydrochloric acid and was extracted three times with ethyl acetate. The organic phase was dried and concentrated to provide crude N-oxide (465 mg). Lithium carbonate (3.1 mmol) in water (28 mL) was added to the crude material and methanol was added in order to effect a solution. The material was then concentrated to approximately 5 mL and was placed on an HP-20 column, eluting with 250 mL each of water, 2.5% aqueous acetone and 5% aqueous acetone to provide the desired product in 93% purity. To further purify, the compound was dissolved in 3.0 mL of 0.05 M lithium carbonate and was chromatographed on an SP-207 column, eluting on a gradient with 0–20% acetone:water, using 300 mL of total solvent. The product fractions that were above 98% purity were combined, concentrated, passed through a millipore filter and lyophilized to provide the desired N-oxide (16 mg, 30%); m.p. >270° C.

Elemental Analysis for $C_{26}H_{19}N_5O_4 \cdot 2Li \cdot 5.43H_2O$

Calc'd: C 54.11; H 5.21; N 12.13;

Found: C 54.50; H 4.71; N 11.74.

EXAMPLE 22

6-Bromo-2-ethyl-3-[[2'-(2H-tetrazol-5-yl)[1,1'-biphenyl]-4-yl]oxy]-4-quinolinecarboxylic acid, dipotassium salt A. 3-[[2'-(Aminocarbonyl)[1,1'-biphenyl]-4-yl]oxy]-6-bromo-2-ethyl-4-quinolinecarboxylic acid A mixture of 5-bromo isatin (0.86 g, 3.81 mmol) and the title A compound of Example 2, 4'-(2-oxobutyloxy)[1,1'-biphenyl]-2-carbonitrile (1.01 g, 3.81 mmol) in 9.5 mL of 30% aq. potassium hydroxide was heated in a 105° C. oil bath for three hours. A very insoluble solid product resulted. This material was directly triturated with excess aq. 1N hydrochloric acid and the solid thus obtained was filtered and washed with water followed by ethyl ether and finally dried in vacuo. The mixture was carried on to the next step without further purification.

B. 6-Bromo-3-[(2'-cyano[1,1'-biphenyl]-4-yl)oxy]-2-ethyl-4-quinolinecarboxylic acid A solution of the title A compound (1.35 g, 2.75 mmol of mixture of isomers) in a mixture of dioxane (6.8 mL) and pyridine (3.4 mL) was cooled to 0° C. and treated with trifluoroacetic anhydride (2.53 g, 1.7 mL, 12.0 mmol). The cold bath was removed and the reaction was stirred at ambient temperature for three hours, then poured into 1N aq. hydrochloric acid and extracted with ethyl acetate. The organic extract was rinsed with water, brine, and dried (magnesium sulfate). Concentration in vacuo gave a crude product (1.5 g). Trituration with ethyl acetate gave the title compound (0.96 g) mixed with another isomer in ca. 72:28 ratio by $^1$H-nmr. This mixture was carried on without further purification.

C. 6-Bromo-2-ethyl-3-[[2'-(2H-tetrazol-5-yl)[1,1'-biphenyl]-4-yl]oxy]-4-quinolinecarboxylic acid The nitrile isomer mixture containing the title B compound (907 mg, 1.92 mmol, ca. 72% desired isomer), $(nBu)_3Sn$—$N_3$ (1.9 g, 5.72 mmol) and xylenes (1 mL) was heated at 107° C. in a stoppered flask for 64 hours. Upon cooling the reaction mixture was dissolved in methylene chloride (2 mL) and flash chromatographed on silica gel (200 g) eluted with 7.5:2:0.5, toluene:acetone:acetic acid. Pooled product fractions gave a desired acid tetrazole (613 mg, 62%) and isomeric by-product (261 mg).

D. 6-Bromo-2-ethyl-3-[[2'-(2H-tetrazol-5-yl)[1,1'-biphenyl]-4-yl]oxy]-4-quinolinecarboxylic acid, dipotassium salt The title C compound (200 mg, 0.387 mmol) was treated with potassium hydroxide (0.85 mL, 1N aq.) and chromatographed on a 20 mL HP-20 column eluted with water. Product containing fractions were pooled and lyophillized to afford the title compound (163 mg, 67%) as a 1.85 water hydrate (does not melt below 260° C.).

Elemental Analysis for $C_{25}H_{16}N_5O_3BrK_2 \cdot 1.85H_2O$

Calc'd: C 47.98; H 3.17; N 11.19; Br 12.77

Found: C 47.59; H 2.73; N 10.89; Br 13.28.

EXAMPLE 23

2-Ethyl-3-[[2'-(2H-tetrazol-5-yl)[1,1'-biphenyl]-4-yl]oxy]-4-quinolinecarboxylic acid, 1-oxide, dilithium salt The title compound of Example 2, 2-ethyl-3-[[2'-(2H-tetrazol-5-yl)[1,1'-biphenyl]-4-yl]oxy]-4-quinolinecarboxylic acid, dilithium salt (98 mg, 0.191 mmol), was dissolved in water (4.5 mL) and then monoperoxyphthalic acid, magnesium salt (MMPP) (309 mg, 0.5 mmol) was added at room temperature. The reaction was then heated to 50° C. and almost all of the material dissolved. Additional MMPP (114 mg) was added after two hours, three hours and four hours (651 mg total) and the reaction was heated for a total of seven hours. The reaction was then acidified by addition of 1 N hydrochloric acid and extracted with ethyl acetate. The organic phase was dried and concentrated. Lithium carbonate (250 mg) in water (25 mL) was then added to the crude mixture and methanol was added in order to effect a solution. Once all of the material dissolved, the solution was concentrated to a volume of approximately 10 mL and the solution was chromatographed on an SP-207 column, eluting with water (200 mL) and then on a gradient from 0–15% acetone:water to provide a slightly impure product (98 mg). This material was flash chromatographed on silica gel, eluting with 87:7:5 ethyl acetate:isopropanol:acetic acid to provide 56 mg of product. This material was dissolved in 1.5 mL of 0.1 M lithium carbonate and methanol (0.5 mL) and was then chromatographed on an HP-20 column, eluting with water (80 mL), then 40 mL each of 5 and 10% acetone:water. The product was concentrated, passed through a millipore filter and lyophilized to provide a white solid (41.9 mg, 48%); m.p. >270° C.

Elemental Analysis for $C_{25}H_{17}N_5O_4 \cdot 2Li \cdot 2.85H_2O$

Calc'd: C 58.12; H 4.43; N 13.55;

Found: C 58.21; H 3.90; N 13.16.

EXAMPLE 24

2-Methyl-3-[[2'-(2H-tetrazol-5-yl) [1,1'-biphenyl]-4-yl]oxy]-4-quinolinecarboxylic acid, dilithium salt A. 4'-(2-Oxopropoxy)[1,1'-biphenyl]-2-carbonitrile The title B compound of Example 1, 4'-hydroxy-[1,1'-biphenyl]-2-carbonitrile (3.00 g, 15.4 mmol) was dissolved in acetone (8 mL) and chloroacetone (1.59 mL, 20.0 mmol), freshly ground potassium carbonate (2.12 g, 15.4 mmol) and potassium iodide (128 mg, 0.77 mmol) were added. The mixture was heated to 60° C. for 15 hours then partitioned between hydrochloric acid (1.0 M) and ethyl acetate. The aqueous phase was extracted with ethyl acetate and the combined organic extracts dried over magnesium sulfate, filtered and the solvent removed to yield a tan solid (4.51 g). This solid was recrystalized from a mixture of toluene and hexane to yield a tan solid (3.34 g, 87%); m.p. 102–105° C.

B. 3-[(2'-Cyano[1,1'-biphenyl]-4-yl)oxy]-2-methyl-4-quinolinecarboxylic acid

Isatin (468 mg, 3.18 mmol) and the title A compound (800 mg, 3.18 mmol) were dissolved in potassium hydroxide (8 mL, 30%) with ethanol (5 mL). The mixture was heated to 75° C. for 1.5 hours then neutralized with hydrochloric acid (1N) and the mixture was extracted with ethyl acetate. The combined organic extracts were dried over magnesium sulfate, filtered and the solvent removed. The residue was purified by flash chromatography using silica gel (150 g) eluted with 1% acetic acid, 19% acetone, toluene. The product containing fractions were combined and the solvent removed to provide a yellow solid (370 mg, 29%); m.p. 217–220° C. (dec).

C. 2-Methyl-3-[[2'-(2H-tetrazol-5-yl)[1,1'-biphenyl]-4-yl]oxy]-4-quinolinecarboxylic acid, dilithium salt The title B compound (400 mg, 1.00 mmol) and tri-n-butyltin azide (1.1 mL, 4.00 mmol) were suspended in xylene (1.1 mL) and the mixture was heated to 105° C. for four days. The mixture was then cooled to room temperature and stirred with methanol for 30 minutes. The reaction mixture was absorbed onto silica gel and purified by flash chromatography using silica gel (150 g) eluted with 5% acetic acid, 30% acetone, toluene. The product containing fractions were combined and the solvent removed to provide a tan solid (290 mg). This solid was dissolved in 1N lithium hydroxide (4.5 mL) with methanol (1 mL) and purified by column chromatography using a 60 mL column volume of HP-20 polystyrene resin eluted with water (200 mL) followed by 100 mL each of 5% and 10% aqueous acetone. The product containing fractions were combined and lyophilized to yield a pale yellow solid (240 mg, 56%); m.p. >270°.

Elemental Analysis for $C_{24}H_{15}N_5O_3Li_2 \cdot 1.32H_2O$
Calc'd: C 62.79; H 3.87; N 15.26;
Found: C 62.79; H 3.82; N 15.09.

EXAMPLE 25

7-Chloro-2-ethyl-3-[[2'-(2H-tetrazol-5-yl)[1,1'-biphenyl]-4-yl]oxy]-4-quinolinecarboxylic acid, ethyl ester, monopotassium salt A. 3-[[2'-(Aminocarbonyl)[1,1'-biphenyl]-4-yl]oxy]-7-chloro-2-ethyl-4-quinolinecarboxylic acid A mixture containing the title A compound of Example 2, 4'-(2-oxobutyloxy)[1,1'-biphenyl]-2-carbonitrile (1.01 g, 3.81 mmol), 6-chloroisatin (692 mg, 3.81 mmol), potassium hydroxide (10 mL, 30% aq.), and ethanol (10 mL) was heated at 82° C. in a stoppered flask overnight. The cooled reaction mixture was next acidified with 6N hydrochloric acid and extracted with ethyl acetate. The organic extract was rinsed with water and brine, dried (magnesium sulfate), and concentrated in vacuo to yield a crude product (2.11 g). This mixture was carried on to the next reaction.

B. 7-Chloro-3-[(2'-cyano[1,1'-biphenyl]-4-yl)oxy]-2-ethyl-4-quinolinecarboxylic acid The crude title A compound (nominally 3.81 mmol) was dissolved in pyridine (20 mL), cooled to 0° C. under argon and treated with trifluoroacetic anhydride (2.69 mL, 4 g, 19.05 mmol). After 30 minutes the reaction appeared to be done. The reaction mixture was acidified with concentrated hydrochloric acid, diluted with water, and extracted with ethyl acetate. The organic extract was rinsed with 1N aq. hydrochloric acid, water, and brine, then dried (magnesium sulfate) and concentrated in vacuo to ca. 2 g of crude product. Flash chromatography on silica gel (200 g) eluted with 5:4:0.1, hexanes:ethyl acetate:acetic acid gave a purified material (0.89 g) which was twice triturated with ethyl ether to yield the title compound (0.54 g, 33%). This material was used directly in the next reaction.

C. 7-Chloro-3-[(2'-cyano[1,1'-biphenyl]-4-yl)oxy]-2-ethyl-4-quinolinecarboxylic acid, ethyl ester The title B compound (540 mg, 1.26 mmol) was dissolved in acetone (4 mL) and treated with ethyl iodide (0.2 mL, 390 mg, 2.50 mmol) and potassium carbonate (522 mg, 3.78 mmol). The reaction mixture was stoppered and stirred at room temperature for 16 hours, then heated at 50° C. for four hours to drive the reaction to completion. The reaction mixture was next cooled to room temperature, diluted with ethyl acetate and filtered. The organic filtrate was rinsed with water, saturated aq. sodium bisulfite, water, and brine, then dried (magnesium sulfate) and concentrated in vacuo to afford a red oil (690 mg). Flash chromatography on silica gel (27 g) yielded the title compound (487 mg, 85%).

D. 7-Chloro-2-ethyl-3-[[2'-(2H-tetrazol-5-yl)[1,1'-biphenyl]-4-yl]oxy]-4-quinolinecarboxylic acid, ethyl ester, monopotassium salt A mixture of the title C compound (467 mg, 1.02 mmol), $(nBu)_3Sn-N_3$ (1.02 g, 3.06 mmol), and xylenes (0.5 mL) was heated at 105° C. in a stoppered flask for 37 hours. After cooling to room temperature, the reaction mixture was treated with methanol, then concentrated in vacuo and flash chromatographed on silica gel (75 g) eluted with 10:4:0.1, hexanes:ethyl acetate:acetic acid to yield a tetrazole product (460 mg, 90%). The ester tetrazole (212 mg, 0.424 mmol) was treated with potassium bicarbonate (42.4 mg, 0.424 mmol) and aq. 1N potassium hydroxide, then chromatographed on HP-20 eluted with a gradient of 0% to 30% aqueous acetone. Product containing fractions were pooled and lyophillized to yield the title compound (148 mg, 62%) as a 1.3 water hydrate (m.p. s150, 218–220° C.).

Elemental Analysis for $C_{27}H_{21}N_5O_3ClK \cdot 1.3H_2O$
Calc'd: C 57.76; H 4.24; N 12.47; Cl 6.31;
Found: C 57.75; H 4.14; N 12.26; Cl 6.04.

EXAMPLE 26

7-Chloro-2-ethyl-3-[[2'-(2H-tetrazol-5-yl)[1,1'-biphenyl]-4-yl]oxy]-4-quinolinecarboxylic acid, dipotassium salt A. 7-Chloro-2-ethyl-3-[[2'-(2H-tetrazol-5-yl)[1,1'-biphenyl]-4-yl]oxy]-4-quinolinecarboxylic acid, ethyl ester Prepared as described for the title D compound of Example 25: 7-Chloro-2-ethyl-3-[[2'-(2H-tetrazol-5-yl)[1,1'-biphenyl]-4-yl]oxy]-4-quinolinecarboxylic acid, ethyl ester, monopotassium salt.

B. 7-Chloro-2-ethyl-3-[[2'-(2H-tetrazol-5-yl)[1,1'-biphenyl]-4-yl]oxy]-4-quinolinecarboxylic acid, dipotassium salt The title A compound (230 mg, 0.46 mmol) was saponified with 1.1 mL of aq. 1N KOH in 2.5 mL of ethanol at 70° C. for 22 hours. After cooling to room temperature, the reaction mixture was directly applied to an 18 mL column of HP-20 which was eluted with a gradient from 0% to 6% aqueous acetone. Product containing fractions were pooled and lyophillized to afford 223 mg of the title compound (85%) as a 1.11 water hydrate (does not melt below 250° C.).

Elemental Analysis for $C_{25}H_{16}N_5O_3ClK_2 \cdot 1.11H_2O$
Calc'd: C 52.85; H 3.33; N 12.22; Cl 6.24;
Found: C 52.85; H 3.33; N 12.22; Cl 6.37.

EXAMPLE 27

2-Propyl-3-[[2'-(2H-tetrazol-5-yl)[1,1'-biphenyl]-4-yl]oxy]-4-quinolinecarboxylic acid, 2-(diethylamino)-2-oxoethyl ester, monopotassium salt A. N,N-Diethylchloroacetamide To a solution of chloroacetic acid (10 g, 0.11 mol) in methylene chloride (530 mL) at 0° C. was added diethylamine hydrochloric acid (15.3 g, 0.14 mol), 1-(3-dimethylaminopropyl)-3-ethyl carbodiimide hydrochloride (26.4 g, 0.14 mol) and 4-methyl morpholine (29 mL, 0.27 mol). After the reaction stirred one hour at 0° C., the reaction was stirred at room temperature for four hours. The reaction mixture was then washed with water, 1N hydrochloric acid (until the aqueous phase was colorless), and saturated sodium chloride, dried over magnesium sulfate, filtered and concentrated to give the title compound as a yellow oil (9.3 g, 58%) which was used directly in the next step.

B. 3-[(2'-Cyano[1,1'-biphenyl]-4-yl)oxy]-2-propyl-4-quinolinecarboxylic acid, 2-(diethylamino)-2-oxoethyl ester To a solution of the title E compound of Example 1, 3-[(2'-cyano[1,1'-biphenyl]-4-yl)oxy]-2-propyl-4-quinolinecarboxylic acid (630 mg, 1.54 mmol) in acetone (5 mL) was added the title A compound (461 mg, 3.08 mmol), potassium carbonate (638 mg, 4.62 mmol), and potassium iodide (50 mg). After stirring at room temperature for 16 hours, the reaction mixture was extracted into ethyl acetate and the organic extract rinsed with water and brine, dried (magnesium sulfate), and concentrated in vacuo. Flash chromatography on silica gel (60 g) eluted with 7:3, hexanes:ethyl acetate failed to purify the product. A second column (110 g silica gel; gradient from 9:1 to 7:3, hexanes:ethyl acetate) yielded the title compound (538 mg, 67%).

C. 2-Propyl-3-[[2'-(2H-tetrazol-5-yl)[1,1'-biphenyl]-4-yl]oxy]-4-quinolinecarboxylic acid, 2-(diethylamino)-2-oxoethyl ester, monopotassium salt A mixture of the title B compound (518 mg, 0.993 mmol), $(nBu)_3Sn-N_3$ (990 mg, 2.98 mmol), and xylenes (0.7 mL) was heated at 110° C. in a stoppered flask for two days. The reaction was cooled to room temperature and flash chromatographed on silica gel (50 g) eluted with first 1 column volume of 6:4, hexanes:ethyl acetate followed by 6:4:0.1, hexanes:ethyl acetate:acetic acid. Product containing fractions were combined to afford a tetrazole product (400 mg, 71%).

The entire product (400 mg, 1.41 mmol) was converted to its potassium salt by treatment with potassium hydroxide (1.69 mL, 1N) followed by chromatography on 35 mL of HP-20 gradient eluted from 0% to 30% aqueous acetone. The product containing fractions were pooled and lyophillized to yield the title compound (234 mg, 54% column yield, 38% overall from the title B compound) as a 0.57 water hydrate; m.p. 118–130° C.

Elemental Analysis for $C_{32}H_{31}N_6O_4K \cdot 0.57H_2O$
Calc'd: C 62.70; H 5.28; N 13.71;
Found: C 62.70; H 5.11; N 13.57.

EXAMPLE 28

2-Cyclopropyl-3-[[2'-(2H-tetrazol-5-yl)[1,1'-biphenyl]-4-yl]oxy]-4-quinolinecarboxylic acid, 2-methyl-1-(1-oxopropoxy)propyl ester, monotpotassium salt A. 2-Cyclopropyl-3-[[2'-[2-(triphenylmethyl)-2H-tetrazol-5-yl][1,1'-biphenyl]-4-yl]oxy]-4-quinolinecarboxylic acid A mixture containing the title compound of Example 6, 2-cyclopropy-3-[[2'-(2H-tetrazol-5-yl)[1,1'-biphenyl]-4-yl]oxy]-4-quinolinecarboxylic acid, dilithium salt (906 mg, 2.02 mmol), triphenylmethyl chloride (590 mg, 2.11 mmol), and triethylamine (0.309 mL, 224 mg, 2.22 mmol) in acetone (10 mL) was stirred at room temperature in a stoppered flask for four days (reaction time beyond two days was unnecessary). The reaction mixture was next filtered and re-dissolved into 40 mL total volume with acetone. Yield was assumed to be 100% and appropriate aliquots were used in subsequent reactions.

B. 2-Cyclopropyl-3-[[2'-[2-(triphenylmethyl)-2H-tetrazol-5-yl][1,1'-biphenyl]-4-yl]oxy]-4-quinolinecarboxylic acid, 2-methyl-1-(1-oxopropoxy)-propyl ester Crude title A compound (nominally 1.21 mmol) and the title A compound of Example 5; propanoic acid, 1-chloro-2-methylpropyl ester (697 mg, 4.23 mmol) were dissolved in dry dimethylformamide (2.4 mL). Potassium carbonate (335 mg, 2.42 mmol), potassium iodide (241 mg, 1.45 mmol), and 18-crown-6 (64 mg, 0.242 mmol) were added and the stoppered reaction mixture was heated at 90° C. for 2.5 hours. After cooling to room temperature, the reaction mixture was diluted with ethyl acetate (50 mL) and filtered. The organic filtrate was rinsed with two 25 mL portions of 5% aq. sodium bisulfite and brine, dried (magnesium sulfate), and concentrated in vacuo to yield a crude product (1.4 g). Flash chromatography on silica gel (50 g) packed in hexanes and eluted with 250 mL of 24:1 followed by ca. 2 L of 12:1, hexanes:ethyl acetate gave the title compound (697 mg, 70% yield overall from the title A compound).

C. 2-Cyclopropyl-3-[[2'-(2H-tetrazol-5-yl)[1,1'-biphenyl]-4-yl]oxy]-4-quinolinecarboxylic acid, 2-methyl-1-(1-oxopropoxy)propyl ester, monopotassium salt The title C compound (667 mg, 0.813 mmol) was dissolved in tetrahydrofuran (16 mL). Absolute ethanol (16 mL) was added, followed by 16 mL of 2N aq. hydrochloric acid, and finally an additional 7 mL of tetrahydrofuran. After 2.5 hours stirring at room temperature, the reaction mixture was adjusted to pH 8 by careful addition of aq. $NaHCO_3$ solution. An attempt to remove precipitated triphenylmethanol at this point was not successful. The total mixture was re-acidified with 2N aq. hydrochloric acid and extracted with ethyl acetate. The organic extract was rinsed with brine, dried (magnesium sulfate), and concentrated in vacuo to give a crude product (668 mg). Flash chromatography on silica gel (50 g) eluted with initially 10:4, hexanes:ethyl acetate followed by 10:4:0.1, hexanes:ethyl acetate:acetic acid gave a product tetrazole (389 mg, 78% yield).

The tetrazole product (0.673 mmol) was treated with potassium bicarbonate (100 mg, 1.01 mmol) in aqueous methanol and chromatographed on 35 mL of HP-20 eluted with a gradient from 0% to 40% aqueous acetone. Product containing fractions were combined and lyophillized to yield the title compound (243 mg, 58%, 48% overall from the title C compound) as a 0.55 water hydrate; m.p. s125, 148–150° C., decomposes.

Elemental Analysis for $C_{33}H_{30}N_5O_5K \cdot 0.55H_2O$
Calc'd: C 63.35; H 5.01; N 11.19;
Found: C 63.35; H 4.90; N 11.21.

EXAMPLE 29

2-Cyclopropyl-3-[[2'-(2H-tetrazol-5-yl)[1,1'-biphenyl]-4-yl]oxy]-1,5-naphthyridine-4-carboxylic acid, dilithium salt A. α-Cyano-3-nitro-2-pyridineacetic acid, ethyl ester Potassium (2.5 g, 63 mmol) was carefully added in small lumps to dry t-butanol (80 mL, distilled from calcium hydride). Upon complete addition, the reaction was warmed to 50° and stirred until all the potassium was consumed.

Ethyl cyanoacetate (6.71 mL, 63 mmol) was added and a thick white precipitate was formed. 2-Chloro-3-nitropyridine (5 g, 31.5 mmol) was added in hot (60° C.) t-butanol (80 mL) and the reaction turned dark orange upon addition. The reaction was heated to reflux for two hours, the t-butanol was removed and the residue partitioned between hydrochloric acid (1N) and ethyl acetate. The aqueous phase was extracted with ethyl acetate and the combined organic phase was dried over magnesium sulfate, filtered and the solvent removed. The brown solid residue was recrystallized from ethyl acetate to give the desired product as red needles (4.8 g, 65%); m.p. 133–134° C.

Elemental Analysis for $C_{10}H_9N_3O_4$
Calc'd: C 51.07; H 3.86; N 17.87;
Found: C 51.09; H 3.68; N 18.00.

B. 3-Amino-α-cyano-2-pyridineacetic acid, ethyl ester

The title A compound (4.8 g, 20.4 mmol) was dissolved in ethanol (750 mL). Palladium on carbon (10%, 200 mg) was added and the reaction mixture hydrogenated under 50 psi. of hydrogen on a Parr shaker apparatus for six hours. The solvent was removed to yield an orange solid which was used directly in the next reaction.

C. 2,3-Dihydro-2-oxo-1H-pyrrolo[3,2-b]pyridine-3-carbonitrile

The title B compound from the previous reaction was suspended in p-xylene (60 mL) and heated to 150° C. in a sealed tube. After 24 hours, the reaction was cooled and the solvent removed to yield a black solid residue that was used directly in the next reaction.

D. 1H-Pyrrolo [3,2-b]pyridin-2(3H)-one

The title C compound from the previous reaction was suspended in concentrated hydrochloric acid (120 mL) and heated to reflux for 24 hours. The reaction mixture was cooled and neutralized with solid potassium carbonate. This solution was extracted with ethyl acetate, the combined extracts dried over magnesium sulfate and the solvent removed to yield 1.82 g (66% over 3 steps) of a brown solid which was used in the next reaction without purification.

E. 3,3-Dibromo-1H-pyrrolo[3,2-b]pyridin-2(3H)-one

The title D compound (181 g, 13.5 mmol) was dissolved in t-butanol (130 mL, 95%) and N-bromosuccinimide (4.8 g, 27 mmol) was added. The reaction was stirred for four hours at room temperature then absorbed onto silica gel (20 g) and purified by flash chromatography on silica gel (350 g) eluted with 30% acetone, hexane to yield the desired product as a tan solid (2.85 g, 72%).

F. 1H-Pyrrolo[3,2-b]pyridine-2,3(3H)-dione

The title E compound (2.78 g, 9.52 mmol) was dissolved in acetonitrile (143 mL) with water (9.5 mL). Silver trifluoroacetate (4.12 g, 19.0 mmol) was added and the mixture was heated to reflux. After one hour, the reaction was cooled to room temperature, filtered through celite to remove the silver bromide and the solvent removed. The residue was absorbed onto silica gel and purified by flash chromatography on silica gel eluted with 50% acetone, hexane to yield the isatin as an orange solid (1.09 g, 77%).

G. 2-Cyclopropyl-3-[[2'-(2H-tetrazol-5-yl)[1,1'-biphenyl]-4-yl]oxy]-1,5-naphthyridine-4-carboxylic acid, dilithium salt The title F compound (246 mg, 1.66 mmol) and the title C compound of Example 6, 1-cyclopropyl-2-[[2'-(2H-tetrazol-5-yl)[1,1'-biphenyl]-4-yl]oxy]ethanone (800 mg, 2.5 mmol) were dissolved in potassium hydroxide (3.2 mL, 30%) with ethanol (1.6 mL). The mixture was heated to 75° C. for 1.5 hours then neutralized with hydrochloric acid (1N). The mixture was extracted with ethyl acetate, the combined organic extracts were dried over magnesium sulfate, filtered and the solvent removed. The residue was absorbed onto silica gel and purified by flash chromatography using silica gel (125 g) eluted with 6% water, 8% acetic acid, ethyl acetate. The product containing fractions were combined and the solvent removed to provide a brown solid (576 g). This residue was dissolved in lithium hydroxide (1M) and purified by column chromatography using HP-20 polystyrene resin (60 mL column volume) eluted with water (200 mL) followed by 100 mL each of 5%, 10% and 15% acetone in water. The product containing fractions were combined and lyophilized to yield a white solid (156 mg) which contained minor impurities by $^1$HNMR. This solid was redissolved in water and repurified by HP-20 resin (60 mL column volume) eluting with 100 mL each of water, 5%, 10% and 15% acetone in water. The product fractions were combined and lyophilized to yield a white solid (120 mg, 11%); m.p. >270°.

Elemental Analysis for $C_{25}H_{16}N_6O_3Li_2 \cdot 1.69H_2O$
Calc'd: C 60.94; H 3.96; N 17.05;
Found: C 61.12; H 3.75; N 16.87.

EXAMPLE 30

2-Cyclopropyl-3-[[2'-(2H-tetrazol-5-yl)[1,1'-biphenyl]-4-yl]oxy]-4-quinolinecarboxylic acid, ethyl ester, monopotassium salt A. 2-Cyclopropyl-3-[[2'-[2-(triphenylmethyl)-2H-tetrazol-5-yl][1,1'-biphenyl]-4-yl]oxy]-4-quinolinecarboxylic acid, ethyl ester A mixture of the title A compound of Example 28, 2-cyclopropyl-3-[[2'-[2-(triphenylmethyl)-2H-tetrazol-5-yl][1,1'-biphenyl]-4-yl]oxy]-4-quinolinecarboxylic acid (372 mg, 0.517 mmol), ethyl iodide (0.13 mL, 254 mg, 1.62 mmol), and potassium carbonate (335 mg, 2.42 mmol) in dimethylformamide (2.5 mL) were heated at 90° C. for 90 minutes. After cooling to room temperature, the reaction mixture was diluted with ethyl acetate and rinsed with aq. 5% sodium bisulfite and brine, dried (magnesium sulfate), and concentrated in vacuo to give a crude product (580 mg). Flash chromatography on silica gel (40 g) eluted with 10:1, hexanes:ethyl acetate yielded the title compound (372 mg, 64%).

B. 2-Cyclopropyl-3-[[2'-(2H-tetrazol-5-yl)[1,1'-biphenyl]-4-yl]oxy]-4-quinolinecarboxylic acid, ethyl ester, monopotassium salt The title A compound (372 mg, 0.517 mmol) was dissolved in tetrahydrofuran (9 mL). Absolute ethanol (9 mL) was added, followed by 9 mL of 2N aq. hydrochloric acid. After three hours stirring at room temperature, the reaction mixture was diluted with ethyl acetate (18 mL) and brine (18 mL). The organic layer was then separated and rinsed with 1:1, water:brine (18 mL) and brine (18 mL), then dried (magnesium sulfate), and concentrated in vacuo to a crude product (377 mg). Flash chromatography on silica gel (30 g) eluted first with 10:4, hexanes:ethyl acetate followed by 10:4:0.1, hexanes:ethyl acetate:acetic acid gave detritylated tetrazole product (189 mg, 76%). The tetrazole (0.396 mmol) was treated 0.52 mL of 1N aq. potassium hydroxide and chromatographed on 15 mL of HP-20 eluted with a gradient from 0% to 30% aqueous acetone. Product containing fractions were combined and lyophillized to yield the title compound (149 mg, 71%, 54% overall from the title A compound) as a 0.86 water hydrate; m.p. s100, 140–150° C., decomposes.

Elemental Analysis for $C_{28}H_{22}N_5O_3K \cdot 0.86\ H_2O$
Calc'd: C 63.32; H 4.50; N 13.19;
Found: C 63.33; H 4.19; N 12.99.

EXAMPLE 31

2-Cyclopropyl-6-methoxy-3-[[2'-(2H-tetrazol-5-yl)
[1,1'-biphenyl]-4-yl]oxy]-4-quinolinecarboxylic
acid, dilithium salt A. 2-Cyclopropyl-6-methoxy-3-[[2'-(2H-tetrazol-5-yl)[1,1'-biphenyl]-4-yl]oxy]-4-quinolinecarboxylic acid, dilithium salt 5-Methoxyindole-2,3-dione (G. B. Bachman, G. M. Picha, *J. Am. Chem. Soc.,* 80, 126 (1958)) (183 mg, 1.03 mmol) and the title C compound of Example 6, 1-cyclopropyl-2-[[2'-(2H-tetrazol-5-yl)[1,1'-biphenyll-4-yl]oxy]-ethanone (300 mg, 0.94 mmol) were dissolved in potassium hydroxide (2 mL, 30%) with ethanol (1 mL).

The mixture was heated to 83° C. for 11 hours then allowed to stand at room temperature for 10 hours. The reaction was then neutralized with hydrochloric acid (1N) and the mixture was extracted with ethyl acetate. The combined organic extracts were dried over magnesium sulfate, filtered and the solvent removed. The residue was purified by flash chromatography using silica gel (65 g) eluted with 5% acetic acid, 15% acetone, toluene. The product containing fractions were combined and the solvent removed to provide a yellow solid (370 mg). This residue was dissolved in lithium hydroxide (1M) and purified by column chromatography using HP-20 polystyrene resin (60 mL column volume) eluted with water (200 mL) followed by 100 mL each of 2.5%, 5%, 10%, 15% and 20% acetone in water. The product containing fractions were combined and lyophilized to yield a light yellow solid (96 mg, 21%); m.p. >270°.

Elemental Analysis for $C_{27}H_{19}N_5O_4Li_2.3.50H_2O$
Calc'd: C 58.49; H 4.73; N 12.63;
Found: C 58.29; H 4.16; N 12.32.

EXAMPLE 32

2-Cyclopropyl-3-[[2'-(2H-tetrazol-5-yl)[1,1'-biphenyl]-4-yl]oxy]-4-quinolinecarboxylic acid, 2-methyl-1-(2,2-dimethyl-1-oxopropoxy)propyl ester, monopotassium salt A. 2-Cyclopropyl-3-[[2'-[2-(triphenylmethyl)-2H-tetrazol-5-yl][1,1'-biphenyl]-4-yl]oxy]-4-quinolinecarboxylic acid, 2-methyl-1-(2,2-dimethyl-1-oxopropoxy)propyl ester A mixture of the title A compound of Example 28, 2-cyclopropyl-3-[[2'-[2-(triphenylmethyl)-2H-tetrazol-5-yl] [1,1'-biphenyl]-4-yl]oxy]-4-quinolinecarboxylic acid (1.55 mmol), the title B compound of Example 16, 2,2-dimethylpropanoic acid, 1-chloro-2-methylpropyl ester (1.09 g, 6.65 mmol), potassium carbonate (521 mg, 3.77 mmol), potassium iodide (375 mg, 2.26 mmol), and 18-crown-6 (100 mg, 0.378 mmol) in dimethylformamide (3.7 mL) was heated at 90° C. for 2.5 hours. After cooling to room temperature, the reaction mixture was diluted with ethyl acetate (75 mL) and filtered. The organic filtrate was rinsed with aq. 5% sodium bisulfite and brine, dried (magnesium sulfate), and concentrated in vacuo to give a crude product (2 g). Flash chromatography on silica gel (60 g) eluted with 1 column volume of hexanes followed by 1.8 L of 12:1, then 900 mL of 8:1, hexanes:ethyl acetate yielded the title compound (950 mg, 72%).

B. 2-Cyclopropyl-3-[[2'-(2H-tetrazol-5-yl)[1,1'-biphenyl]-4-yl]oxy]-4-quinolinecarboxylic acid, 2-methyl-1-(2,2-dimethyl-1-oxopropoxy)propyl ester, monopotassium salt The title A compound (930 mg, 1.10 mmol) was dissolved in tetrahydrofuran (22 mL). Absolute ethanol (22 mL) was added, followed by 22 mL of 2N aq. hydrochloric acid. After two hours stirring at room temperature, the reaction mixture was diluted with ethyl acetate (100 mL), transferred to a separatory funnel, rinsed with three 50 mL portions of brine, dried (magnesium sulfate), and concentrated in vacuo to give 2 g of crude product. Flash chromatography on silica gel (70 g) eluted first with 10:4, hexanes:ethyl acetate followed by 10:4:0.1, hexanes:ethyl acetate:acetic acid gave detritylated tetrazole product (580 mg, 87%). The tetrazole (0.96 mmol) was treated with excess potassium bicarbonate and chromatographed on 35 mL of HP-20 eluted with a gradient from 0% to 70% aqueous acetone. Product containing fractions were combined and lyophillized to yield the title compound (340 mg, 54%, 47% overall from the title B compound) as a 0.9 water hydrate; m.p. s78, 86–123° C.).

Elemental Analysis for $C_{35}H_{34}N_5O_5K.0.9H_2O$
Calc'd: C 63.69; H 5.47; N 10.61;
Found: C 64.13; H 5.77; N 10.17.

EXAMPLE 33

2-Cyclopropyl-3-[[2'-(2H-tetrazol-5-yl)[1,1'-biphenyl]-4-yl]oxy]-4-quinolinecarboxylic acid, 1-(1-oxopropoxy)-ethyl ester, monopotassium salt A. Propanoic acid, 1-chloroethyl ester Zinc chloride (75 mg) was fused in a dry flask. Propanoyl chloride (43.4 mL, 0.500 mol) and dry methylene chloride (30 mL) were added and the mixture cooled to 0° C. under argon. Acetaldehyde (27.95 mL, 0.500 mol) was added to the reaction mixture at a rate that kept the internal temperature between 10 and 15° C. The bath was removed and the reaction stirred at ambient temperature for two hours. After carefully concentrating the reaction mixture on a rotary evaporator, the residue was distilled to provide the title compound (8 g, 12%) which distilled at 30° C. at less than 1 mm Hg pressure.

B. 2-Cyclopropyl-3-[[2'-[2-(triphenylmethyl)-2H-tetrazol-5-yl][1,1'-biphenyl]-4-yl]oxy]-4-quinolinecarboxylic acid, 1-(1-oxopropoxy)ethyl ester A mixture of the title A compound of Example 28, 2-cyclopropyl-3-[[2'-[2-(triphenylmethyl)-2H-tetrazol-5-yl] [1,1'-biphenyl]-4-yl]oxy]-4-quinolinecarboxylic acid (1.55 mmol), the title A compound (1.1 g, 8.05 mmol), potassium carbonate (521 mg, 3.77 mmol), potassium iodide (375 mg, 2.26 mmol), and 18-crown-6 (100 mg, 0.378 mmol) in dimethylformamide (3.7 mL) were heated at 65° C. for 45 minutes. After cooling to room temperature, the reaction mixture was diluted with ethyl acetate (75 mL) and filtered. The organic filtrate was rinsed with aq. 5% sodium bisulfite and brine, dried (magnesium sulfate), and concentrated in vacuo to give a crude product (2 g). Flash chromatography on silica gel (50 g) eluted with 1 column volume of hexanes followed by 1.8 L of 6:1, hexanes:ethyl acetate yielded the title compound (930 mg, 76%).

C. 2-Cyclopropyl-3-[[2'-(2H-tetrazol-5-yl)[1,1'-biphenyl]-4-yl]oxy]-4-quinolinecarboxylic acid, 1-(1-oxopropoxy)ethyl ester, monopotassium salt The title B compound (830 mg, 1.04 mmol) was dissolved in tetrahydrofuran (20 mL). Absolute ethanol (20 mL) was added, followed by 20 mL of 2N aq. hydrochloric acid. After two hours stirring at room temperature, the reaction mixture was diluted with ethyl acetate (100 mL), transferred to a separatory funnel, rinsed with three 50 mL portions of brine, dried (magnesium sulfate), and concentrated in vacuo to ca. 1 g of crude product. The crude product was combined with material from a 100 mg pilot reaction carried out in exactly the same manner (total starting material: 930 mg, 1.17 mmol). Flash chromatography on silica gel (70 g) eluted first with 10:4, hexanes:ethyl acetate followed by 15:5:0.12, hexanes:ethyl acetate:acetic acid gave detritylated tetrazole product (450 mg, 70%). The tetrazole (435 mg, 0.792 mmol) was treated with excess potassium bicarbonate and chromatographed on an HP-20 column eluted with a gradient from 0% to 40% aqueous acetone. Product containing fractions were combined and lyophillized to yield the title compound (259 mg, 54%, 37% overall from the title B compound) as a 0.9 water hydrate; m.p. 100–155° C.

Elemental Analysis for $C_{31}H_{26}N_5O_5K \cdot 0.9H_2O$
Calc'd: C 61.66; H 4.64; N 11.60;
Found: C 61.68; H 4.41; N 11.40.

EXAMPLE 34

2-Propyl-3-([2'-(2H-tetrazol-5-yl)[1,1'-biphenyl]-4-yl]oxy]-4-quinolinecarboxylic acid, 2-methyl-1-(2, 2-dimethyl-1-oxopropoxy)propyl ester A. 2-Propyl-3-[[2'-(2H-tetrazol-5-yl)[1,1'-biphenyl]-4-yl]oxy]-4-quinolinecarboxylic acid A solution of the title E compound of Example 1, 3-[(2'-cyano[1,1'-biphenyl]-4-yl)oxy]-2-propyl-4-quinolinecarboxylic acid (3.9 g, 9.6 mmol) and tri-n-butyltin azide (9.6 g, 28.9 mmol) in o-xylene (3.9 mL) was heated to 108° C. for 48 hours. After cooling to room temperature, methanol (15 mL) was added and the dark brown solution was stirred for 20 minutes. The methanol was removed under vacuum, more methanol was added (15 mL), the reaction mixture was stirred briefly and concentrated again. The residue was dissolved in ethyl acetate (500 mL), washed three times with 1.0M trisodium citrate solution, brine, dried over sodium sulfate, and concentrated to yield a brown, viscous oil (10.98 g). Flash chromatography on silica gel (659 g), eluting with 70:25:5 toluene:acetone:acetic acid yielded the title compound as a light yellow solid 2.14 g).

B. 2-Propyl-3-[[2'-[2-(triphenylmethyl)-2H-tetrazol-5-yl][1,1'-biphenyl]-4-yl]oxy]-4-quinolinecarboxylic acid A solution of the title A compound (1.5 g, 3.3 mmol), triphenylmethyl chloride (0.97 g, 3.5 mmol), and triethylamine (0.51 mL, 3.7 mmol) in acetone (17 mL) was stirred at room temperature for 16 hours. The reaction mixture was diluted with acetone (50 mL); triethylammonium hydrochloride was collected by filtration and rinsed with several portions of acetone. The filtrate was concentrated, the residue was dissolved in ethyl acetate (60 mL), washed three times with water (20 mL each) and brine. The combined aqueous layers were back-extracted with ethyl acetate, the combined ethyl acetate layers were dried over sodium sulfate and evaporated in vacuo to yield a solid. TLC (silica, 90:5:5 ethyl acetate:methanol:acetic acid) indicated the presence of the title A compound in the combined aqueous layers. The crude product was flash-chromatographed, eluting with 95:5 ethyl acetate:hexanes yielded the title compound (0.32 g, 14%) as a white solid, mp 167–170° C. with foaming.

C. 2-Propyl-3-[[2'-[2-(triphenylmethyl)-2H-tetrazol-5-yl][1,1'-biphenyl]-4-yl]oxy]-4-quinolinecarboxylic acid, 2-methyl-1-(2,2-dimethyl-1-oxopropoxy)propyl ester A mixture of the title B compound (0.42 g, 0.61 mmol), the title B compound of Example 16, 2,2-dimethylpropanoic acid, 1-chloro-2-methylpropyl ester (0.39 g, 2.0 mmol), KI (0.12 g, 0.73 mmol), potassium carbonate (0.17 g, 1.2 mmol), and 18-Crown-6 (0.03 g, 0.12 mmol) in dimethylformamide (1.2 mL) was stirred at 90° C. for 2.5 hours. After standing for 16 hours at room temperature, ethyl acetate (40 mL) was added, the insoluble salts were removed by filtration, the filtrate was washed with 50% aqueous sodium sulfite solution, water, brine, dried over sodium sulfate, and concentrated to yield a light brown, viscous oil (0.48 g). Flash chromatography on silica gel (35 g), eluting with 95:5 hexanes:ethyl acetate yielded the title compound (0.23 g, 44%) as a white solid; m.p. 68–140° C. with foaming.

D. 2-Propyl-3-[[2'-(2H-tetrazol-5-yl)[1,1'-biphenyl]-4-yl]oxy]-4-quinolinecarboxylic acid, 2-methyl-1-(2,2-dimethyl-1-oxopropoxy)propyl ester A solution of the title C compound (0.23 g, 0.27 mmol) in ethanol (5.4 mL) and tetrahydrofuran (5.4 mL) was treated with 5.4 mL of 2M hydrochloric acid. Stirring was continued for three hours. The reaction was quenched by the addition of ethyl acetate (60 mL) and 40 mL of 1:1 water:brine. The ethyl acetate layer was washed with 40 mL of 1:1 water:brine, dried over sodium sulfate, and concentrated to yield 0.21 g of crude product. Flash chromatography on silica gel (10 g) eluting with 0.5 L of hexane, 1 L of 95:5 hexane: ethyl acetate, 0.5 L of 85:15 hexane:ethyl acetate, 0.5 L of 75:25 hexane:ethyl acetate, and 1.0 L of 75:23:2 hexane:ethyl acetate:acetic acid yielded the title compound as a white solid (0.16 g, 97%); m.p. 68–130° C. with foaming.

E. 2-Propyl-3-[[2'-(2H-tetrazol-5-yl)[1,1'-biphenyl]-4-yl]oxy]-4-quinolinecarboxylic acid, 2-methyl-1-(2,2-dimethyl-1-oxopropoxy)propyl ester A solution of the title D compound (0.15 g, 0.25 mmol) in tetrahydrofuran (0.87 mL, room temperature) was treated with potassium bicarbonate (29.6 mg, 0.30 mmol) and water (0.65 mL). After 15 minutes, tetrahydrofuran was removed under vacuum. The residue was purified by preparative HPLC on a 30×500 mm YMC S-10 ODS column eluted with 90:10:0.1, methanol:water:TFA to yield the title compound as a white solid (78.2 mg, 46%); m.p. 78–93° C. with foaming.

Elemental Analysis for $C_{35}H_{37}N_5O_5 \cdot 1.0C_2HF_3O_2$
Calc'd: C 61.66; H 5.17; N 9.72;
Found: C 61.53; H 5.19; N 9.72.

EXAMPLE 35

2-Ethyl-3-[[2'-(2H-tetrazol-5-yl)[1,1'-biphenyl]-4-yl]oxy]-4-quinolinecarboxylic acid, ethyl ester, monopotassium salt A. 3-[(2'-Cyano[1,1'-biphenyl]-4-yl)oxy]-2-ethyl-4-quinolinecarboxylic acid, ethyl ester A mixture containing the title C compound of Example 2, 3-[(2'-cyano[1,1'-biphenyl]-4-yl)oxy]-2-ethyl-4-quinolinecarboxylic acid (707 mg, 1.79 mmol), ethyl iodide (559 mg, 3.58 mmol), and cesium carbonate (1.46 g, 4.48 mmol) in dimethylformamide (4 mL) was stirred at room temperature for nine hours, then diluted with a mixture of acetone and ethyl acetate and filtered. The filtrate was concentrated in vacuo and the product extracted into ethyl acetate. The organic extract was rinsed with water and brine, dried (magnesium sulfate), and concentrated in vacuo to afford a crude product (720 mg). Flash chromatography on Merck silica gel (30 g) eluted with 1:1 hexanes:ethyl acetate afforded the title compound (703 mg, 93% yield).

B. 2-Ethyl-3-[[2'-(2H-tetrazxol-5-yl)[1,1'-biphenyl]-4-yl]oxy]-4-quinolinecarboxylic acid, ethyl ester, monopotassium salt A mixture of the title A compound (700 mg, 1.66 mmol), tributyltin azide (2.2 g, 6.64 mmol), and xylenes (1 mL) was heated in a stoppered flask at 105° C. for 24 hours, then treated with an additional 1 g of tributyltin azide and re-heated for 24 hours. A final quantity of azide reagent (0.5 g) was added and heating continued for another 16 hours. The reaction mixture was then cooled and treated with methanol (2 mL), stirred for 30 minutes, and concentrated in vacuo. Flash chromatography on Merck silica gel (100 g) eluted with 10:4:0.1 hexanes:ethyl acetate:acetic acid followed by 8:4:0.1 hexanes:ethyl acetate:acetic acid yielded a tetrazole product (686 mg, 89% yield). A portion of this product (250 mg, 0.537 mmol) was dissolved in ethanol and treated with potassium bicarbonate (64.5 mg, 0.644 mmol) dissolved in water and the resulting solution of potassium salt was purified on a 25 mL HP-20 polystyrene resin column eluted with an acetone-water gradient. Product fractions eluting between 20 and 30 percent acetone were pooled and concentrated in vacuo. Lyophillization yielded 180 mg (58% overall yield) of tetrazole potassium salt (the title compound). m.p. 227–234° C.

Elemental Analysis for $C_{27}H_{22}N_5O_3K \cdot 0.8H_2O$
Calc'd: C 62.60; H 4.59; N 13.52;
Found: C 62.42; H 4.00; N 13.21.

EXAMPLE 36

2-Cyclopropyl-3-[[2'-(2H-tetrazol-5-yl)[1,1'-biphenyl]-4-yl]oxy]-1,8-naphthyridine-4-carboxylic acid, dilithium salt A. 3,3-Dibromo-1,3-dihydro-2H-pyrrolo[2,3-b]-pyridin-2-one 7-Azaindole (4.08 g, 34.5 mmol) was dissolved in t-butanol (250 mL) and water (3 mL) and pyridinium bromide perbromide (34.2 g, 107 mmol) was slowly added, portionwise over the course of 45 minutes. upon full addition, a light yellow precipitate had started to form. The reaction was stirred a room temperature for five hours and then water (5 mL) was added to the stirring reaction and the reaction was concentrated in vacuo. The crude material was then partitioned between water and ethyl acetate and the organic extracts were washed two times with water and once with brine. The pH of the aqueous phase at this time was 5. The organic phase was then dried and concentrated to provide a tan solid (9.67 g, 96%).

B. 1H-Pyrrolo[2,3-b]pyridine-2,3-dione

The title A compound (3.0 g, 10.3 mmol) was dissolved in acetonitrile (155 mL) and water (10.4 mL) and then silver trifluoroacetate (4.6 g, 20.6 mmol) was added and the reaction was shielded from light and heated to 85° C. for 1.5 hours. The reaction was then cooled and filtered through a pad of celite, rinsing the pad with acetonitrile. The filtrate was concentrated and the residue was partitioned between water and methylene chloride and the organics were dried and concentrated to provide a crude material (0.417 g). The crude material was flash chromatographed (silica gel, 55:45 hexane:ethyl acetate) to provide 252 mg (60% column recovery, 17% overall) of the pure azaisatin.

C. 2-Cyclopropyl-3-[[2'-(2H-tetrazol-5-yl)-[1,1'-biphenyl]-4-yl]oxy]-1,8-naphthyridine-4-carboxylic acid The title B compound (195 mg, 1.32 mmol) and the title C compound of Example 6, 1-cyclopropyl-2-[[2'-(2H-tetrazol-5-yl)-[1,1'-biphenyl]-4-yl]oxy]ethanone (1.27 g, 3.95 mmol) were dissolved in potassium hydroxide (2.5 mL, 30%) and ethanol (1.25 mL) and the reaction was tightly sealed and heated to 80° C. in a preheated oil bath for 45 minutes. The reaction was cooled and the ethanol was removed in vacuo. Water was added and the pH was made acidic by the addition of 1 N hydrochloric acid. The reaction was extracted with ethyl acetate and a mixture of methanol/methylene chloride. The organics were combined, dried and concentrated to provide a crude yellow solid which was preabsorbed on silica gel and was flash chromatographed on silica gel, eluting first with ethyl acetate to elute the excess of the title C compound of Example 6 that was used, and then using 86:8:6 ethyl acetate:acetic acid: water to elute the product. The product fractions were concentrated and azeotroped with toluene and hexane to provide the desired product (480 mg, 81%).

D. 2-Cyclopropyl-3-[[2'-(2H-tetrazol-5-yl)-[1,1'-biphenyl]-4-yl]oxy]-1,8-naphthyridine-4-carboxylic acid, dilithium salt An aqueous solution of 1.0 M lithium hydroxide (2.4 mL) was added to the title C compound (480 mg, 1.07 mmol) and methanol (5 mL) was added in order to effect a solution. The solution was chromatographed on an HP-20 column, eluting with water (500 mL), followed by 5% acetone:water. The product was concentrated, passed through a millipore filter and lyophilized to provide the desired product as a white solid (442 mg, 89%); m.p. >255° C.

Elemental Analysis for $C_{25}H_{16}N_6O_3 \cdot 2Li \cdot 0.91H_2O$
Calc'd: C 62.72; H 3.75; N 17.56;
Found: C 63.05; H 3.43; N 17.23.

EXAMPLE 37

2-Cyclopropyl-5-methyl-3-[[2'-(2H-tetrazol-5-yl)-[1,1'-biphenyl]-4-yl]oxy]-4-quinolinecarboxylic acid, dilithium salt A. 2-Methyl-6-nitro-α-oxobenzenepropanoic acid Sodium metal (3.80 g, 165 mmol) was dissolved in absolute ethanol (66 mL) at 0° C. The 3-nitro-o-xylene (10 g, 66.2 mmol) and diethyl oxalate (18 mL, 132 mmol) were then added and the reaction was warmed to room temperature and stirred for 18 hours. The reaction was refluxed for 30 minutes, then cooled and water (22 mL) was added and the reaction was stirred at room temperature for one hour. The reaction was concentrated to remove the ethanol, then extracted with ethyl acetate, washed with brine, dried over sodium sulfate, filtered and concentrated to provide the desired product (13.92 g, 94%).

B. 2-Methy-6-nitrobenzeneacetic acid

The title A compound (13.92 g, 62.4 mmol) was dissolved in 1N sodium hydroxide (187 mL) at 0° C. and 30% hydrogen peroxide (7.8 mL, 68.6 mmol) was added dropwise and the reaction was stirred at 0° C. for 90 minutes. The reaction was then acidified to pH=2 by the addition of 10% aqueous hydrochloric acid and stirred for an hour at room temperature, then the solid was filtered off and washed with water. The solid was recrystallized from ethyl acetate:hexane to provide the desired acid (5.99 g, 49%).

C. 1,3-Dihydro-4-methyl-2H-indol-2-one

The title B compound (6.54 g, 33.5 mmol) was dissolved in ethanol (200 mL) and 50% aqueous sulfuric acid (134 mL) and heated to 90° C. Zinc metal (8.77 g, 134 mmol) was added to the reaction at 90° C. over one hour and stirred an additional hour after full addition. The reaction was then cooled, filtered and concentrated to remove the ethanol. The residue was partitioned between water and 1:1 chloroform-:ethyl acetate and the organic phase was washed with saturated sodium bicarbonate and brine, then dried over sodium sulfate, filtered and concentrated to provide the desired oxindole (2.91 g, 59%).

D. 4-Methyl-1H-indole-2,3-dione

The title C compound was heated to 50° C. in ethanol (275 mL) until all of the material went into solution. The reaction was then cooled to 40° C. and sodium nitrite (1.22 g, 17.6 mmol) was added, followed by a slow addition of concentrated hydrochloric acid (4.0 mL). Upon full addition, the reaction was heated at 40° C. for 16 hours. The reaction was cooled, concentrated in vacuo and then water was added to the residue and the pH was adjusted to 6–7 by the addition of saturated sodium bicarbonate solution. The reaction was extracted with ethyl acetate, the organic phase was washed with water, dried and concentrated to provide a crude yellow-orange solid (1.21 g). The material was purified by flash chromatography (silica gel, 80:18:2 hexane:ethyl acetate:acetic acid) to provide the desired product as an orange solid (0.390 g, 36%).

E. 2-Cyclopropyl-5-methyl-3-[[2'-(2H-tetrazol-5-yl)[1,1'-biphenyl]-4-yl]oxy]-4-quinolinecarboxylic acid dilithium salt The title D compound (300 mg, 1.86 mmol) was dissolved in 30% Potassium hydroxide solution (4.0 mL) and the title C compound of Example 6, 1-cyclopropyl-2-[[2'-(2H-tetrazol-5-yl)-[1,1'-biphenyl]-4-yl]oxy]ethanone (596 mg, 1.86 mmol) was added and the reaction was heated to 110° C. for 19 hours. The reaction was then cooled and water was added, along with concentrated hydrochloric acid until pH=1. The mixture was then extracted with ethyl acetate, dried and concentrated to provide a crude yellow-brown solid (0.88 g). The crude material was combined with another 0.169 g of crude material from a previous reaction and the combined materials were preabsorbed on silica gel and flash chromatographed (silica gel, 50:50 ethyl acetate:hexane) to provide 0.420 g of 88% pure product by HPLC. Lithium hydroxide (4.2 mL, 1.0M) was added to the mixture and the solution was chromatographed on an HP-20 column, eluting with water (250 mL), followed by a 0–25% acetone:water gradient elution using 1.5 L of total solvent. The product fractions were concentrated, then water and activated carbon were added and the material heated on a steam bath for ten minutes. The solution was filtered through a millipore filter equipped with a celite pad to retain the charcoal and was lyophilized to provide the pure tetrazole (180 mg, 21%); m.p. >270° C.

Elemental Analysis for $C_{27}H_{19}N_5O_3Li_2 \cdot 2.74H_2O$
Calc'd: C 61.80; H 4.70; N 13.35;
Found: C 61.93; H 4.81; N 13.22.

What is claimed is:

1. A compound of the formula I

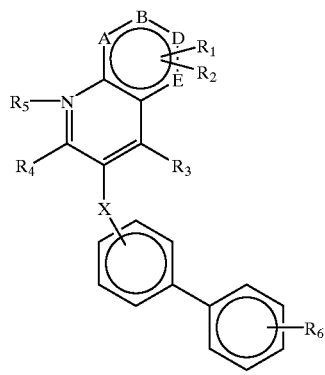

or pharmaceutically acceptable salts thereof;
wherein
A, B, D and E are each carbon atoms;
X is —O—, —S—, —SO— or —SO$_2$—;
R$_1$ and R$_2$ are substituents on A, B, D or E when A, B, D or E are carbon and are independently selected from hydrogen; alkyl of 1 to 4 carbon atoms optionally substituted with substituents selected from amino, hydroxy or alkoxy of 1 to 4 carbon atoms; alkoxy of 1 to 4 carbon atoms, halogen; hydroxy; haloalkyl; cyano; nitro; amino; alkylamino or dialkylamino of up to 6 carbon atoms; (dialkylamino)alkyl of 3 to 8 carbon atoms; alkanoyl of 1 to 4 carbon atoms; carbamoyl; (N-alkyl)carbamoyl or di(N-alkyl)carbamoyl of up to 7 carbon atoms; carboxy; alkoxycarbonyl of 1 to 4 carbon atoms; alkylthio of 1 to 6 carbon atoms; alkylsulphinyl of 1 to 6 carbon atoms; alkylsulphonyl of 1 to 6 carbon atoms;

R$_3$ is —CO$_2$H, —CO$_2$R$_7$, —CHO, —CONHOR$_{10}$, —CONHR$_8$, —CONR$_8$R$_8$', —CONH$_2$ or —CONHSO$_2$CF$_3$;

R$_4$ is hydrogen, alkyl, alkenyl, alkynyl, arylalkyl, cycloalkyl, (cycloalkyl)alkyl, phenyl, or an alkyl substituted with 1 or more fluorine atoms;

R$_5$ is an optional oxygen atom;

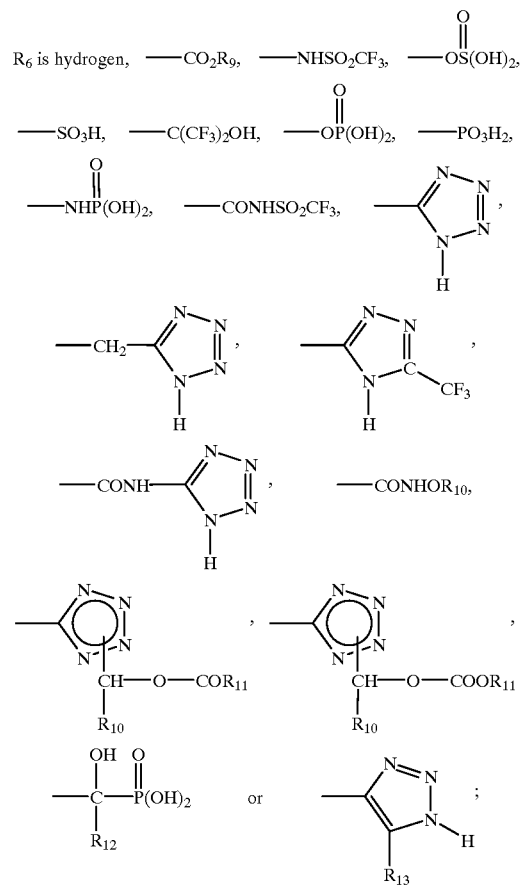

R$_7$ is alkyl, aryl, arylalkyl, aryloxyalkyl, —CH$_2$—COOR$_8$

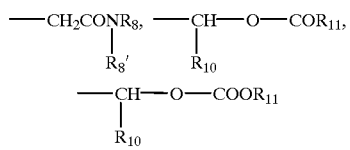

or indanyl;

R$_8$ and R$_8$' are independently a lower alkyl;

R$_9$ is hydrogen, alkyl, perfluoroalkyl of 1 to 8 carbon atoms, cycloalkyl of 3 to 6 carbon atoms, phenyl, benzyl

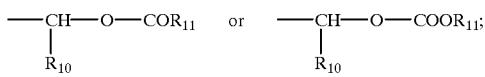

$R_{10}$ is hydrogen, alkyl, aryl, arylalkyl or cycloalkyl;
$R_{11}$ is alkyl, aryl, arylalkyl or cycloalkyl;
$R_{12}$ is hydrogen, alkyl of 1 to 5 carbon atoms or phenyl;
$R_{13}$ is —CN, —NO$_2$ or —CO$_2$R$_9$;
the term "alkyl" refers to both straight and branched chain groups having 1 to 10 carbon atoms;
the term "alkenyl" and "alkynyl" refer to both straight and branched chain groups having 2 to 10 carbon atoms;
the term "aryl" refers to phenyl or naphthyl or phenyl or naphthyl substituted with one or more substituents selected from halogen, alkyl, alkoxy, carboxy, alkylthio, hydroxy, alkanoyl, nitro, amino, alkylamino, dialkylamino or trifluoromethyl groups; and
the term "cycloalkyl" refers to groups having 3 to 8 carbon atoms.

2. A compound of claim 1 wherein
$R_1$ and $R_2$ are independently hydrogen, methyl, methoxy, chlorine or bromine;
$R_3$ is —COOH, —COOR$_7$ where R$_7$ is ethyl, propyl, butyl,

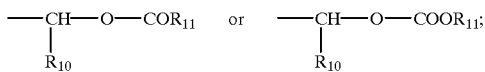

where
$R_{10}$ and $R_{11}$ are independently methyl, ethyl, isopropyl or t-butyl;
$R_4$ is methyl, ethyl, propyl, butyl, pentyl, cyclopropyl, trifluoromethyl, or pentafluoroethyl;
$R_5$ is absent or is oxygen;
$R_6$ is 5-tetrazolyl,

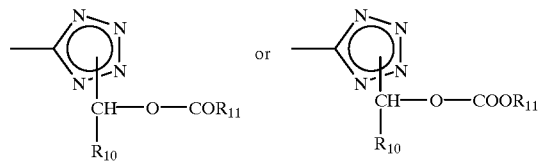

where
$R_{10}$ and $R_{11}$ are defined as above;
X is oxygen, sulfur or —SO$_2$; and
A, B, D and E are all carbon.

3. A compound of claim 1 wherein
$R_1$ and $R_2$ are independently hydrogen, bromine or chlorine;
$R_3$ is —COOH or —COOR$_7$ where R$_7$ is

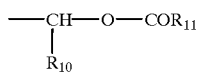

where
$R_{10}$ is methyl or isopropyl and $R_{11}$ is methyl, ethyl, t-butyl or isopropyl;
$R_4$ is methyl, ethyl, propyl, cyclopropyl or trifluoromethyl;

$R_5$ is absent or is oxygen;
$R_6$ is 5-tetrazolyl;
X is oxygen; and
A, B, D and E are all carbon.

4. A compound of claim 1, 2-Propyl-3-[[2'-(2H-tetrazol-5-yl)[1,1'-biphenyl]-4-yl]oxy]-4-quinolinecarboxylic acid, or a pharmaceutically acceptable salt thereof.

5. A compound of claim 1, 2-Ethyl-3-[[2'-(2H-tetrazol-5-yl)[1,1'-biphenyl]-4-yl]-oxy]-4-quinolinecarboxylic acid, or a pharmaceutically acceptable salt thereof.

6. A compound of claim 1, 2-Propyl-3-[[2'-(2H-tetrazol-5-yl)[1,1'-biphenyl]-4-yl]oxy]-4-quinolinecarboxylic acid, ethyl ester, or a pharmaceutically acceptable salt thereof.

7. A compound of claim 1, 2-Propyl-3-[[2'-(2H-tetrazol-5-yl)[1,1'-biphenyl]-4-yl]oxy]-4-quinolinecarboxylic acid, ethyl ester, 1-oxide, or a pharmaceutically acceptable salt thereof.

8. A compound of claim 1, 2-Propyl-3-[[2'-(2H-tetrazol-5-yl)[1,1'-biphenyl]-4-yl]oxy]-4-quinolinecarboxylic acid, 2-methyl-1-(1-oxopropoxy)propyl ester, or a pharmaceutically acceptable salt thereof.

9. A compound of claim 1, 2-Cyclopropyl-3-[[2'-(2H-tetrazol-5-yl)[1,1'-biphenyl]-4-yl]oxy]-4-quinolinecarboxylic acid, or a pharmaceutically acceptable salt thereof.

10. A compound of claim 1, 2-Ethyl-3-[2'-(2H-tetrazol-5-yl)[1,1'-biphenyl]-4-yl]oxy]-4-quinolinecarboxylic acid, 2-methyl-1-(1-oxopropoxy)propyl ester, or a pharmaceutically acceptable salt thereof.

11. A compound of claim 1, 7-Chloro-2-(cyclopropyl)-3-[[2'-(2H-tetrazol-5-yl)[1,1'-biphenyl]-4-yl]oxy]-4-quinolinecarboxylic acid, or a pharmaceutically acceptable salt thereof.

12. A compound of claim 1, 2-Cyclopropyl-6-fluoro-3-[[2'-(2H-tetrazol-5-yl-[1,1'-biphenyl]-4-yl]oxy]-4-quinolinecarboxylic acid, or a pharmaceutically acceptable salt thereof.

13. A compound of claim 1, 2-Cyclopropyl-8-methyl-3-[[2'-(2H-tetrazol-5-yl)[1,1'-biphenyl]-4-yl]oxy]-4-quinolinecarboxylic acid, or a pharmaceutically acceptable salt thereof.

14. A compound of claim 1, 2-Cyclopropyl-3-[[2'-(2H-tetrazol-5-yl)[1,1'-biphenyl]-4-yl]oxy]-4,5-quinolinedicarboxylic acid, or a pharmaceutically acceptable salt thereof.

15. A compound of claim 1, 2-Propyl-3-[[2'-(1H-tetrazol-5-yl)[1,1'-biphenyl]-4-yl]oxy]-4-quinolinecarboxylic acid, butyl ester, or a pharmaceutically acceptable salt thereof.

16. A compound of claim 1, 2-Propyl-3-[[2'-(1H-tetrazol-5-yl)[1,1'-biphenyl]-4-yl]oxy]-4-quinolinecarboxylic acid, 2-(1,1-dimethylethoxy)-2-oxoethyl ester, or a pharmaceutically acceptable salt thereof.

17. A compound of claim 1, 2-Ethyl-3-[[2'-(1H-tetrazol-5-yl)[1,1'-biphenyl]-4-yl]oxy]-4-quinolinecarboxylic acid, 2-(1,1-dimethylethoxy)-2-oxoethyl ester, or a pharmaceutically acceptable salt thereof.

18. A compound of claim 1, 2-Ethyl-3-[[2'-(1H-tetrazol-5-yl)[1,1'-biphenyl]-4-yl]oxy]-4-quinolinecarboxylic acid, butyl ester, or a pharmaceutically acceptable salt thereof.

19. A compound of claim 1, 2-Ethyl-3-[[2'-(1H-tetrazol-5-yl)[1,1'-biphenyl]-4-yl]oxy]-4-quinolinecarboxylic acid, 1-(2,2-dimethyl-1-oxopropoxy)-2-methylpropyl ester, or a pharmaceutically acceptable salt thereof.

20. A compound of claim 1, 2-Cyclopropyl-3-[[2'-[2-[1-(2,2-dimethyl-1-oxopropoxy)-2-methylpropyl]-2H-tetrazol-5-yl][1,1'-biphenyl]-4-yl]oxy]-4-quinolinecarboxylic acid, or a pharmaceutically acceptable salt thereof.

21. A compound of claim 1, 2-Cyclopropyl-3-[[2'-(2H-tetrazol-5-yl)[1,1'-biphenyl]-4-yl]oxy]-4-quinolinecarboxylic acid, (5-methyl-2-oxo-1,3-dioxol-4-yl) methyl ester, or a pharmaceutically acceptable salt thereof.

22. A compound of claim 1, 6-Bromo-2-propyl-3-[[2'-(2H-tetrazol-5-yl)[1,1'-biphenyl]-4-yl]oxy]-4-quinolinecarboxylic acid, or a pharmaceutically acceptable salt thereof.

23. A compound of claim 1, 2-Propyl-3-[[2'-(2H-tetrazol-5-yl)[1,1'-biphenyl]-4-yl]oxy]-4-quinolinecarboxylic acid, 1-oxide, or a pharmaceutically acceptable salt thereof.

24. A compound of claim 1, 6-Bromo-2-ethyl-3-[[2'-(2H-tetrazol-5-yl)[1,1'-biphenyl]-4-yl]oxy]-4-quinolinecarboxylic acid, or a pharmaceutically acceptable salt thereof.

25. A compound of claim 1, 2-Ethyl-3-[[2'-(2H-tetrazol-5-yl)[1,1'-biphenyl]-4-yl]oxy]-4-quinolinecarboxylic acid, 1-oxide, or a pharmaceutically acceptable salt thereof.

26. A compound of claim 1, 2-Methyl-3-[[2'-(2H-tetrazol-5-yl)[1,1'-biphenyl]-4-yl]oxy]-4-quinolinecarboxylic acid, or a pharmaceutically acceptable salt thereof.

27. A compound of claim 1, 7-Chloro-2-ethyl-3-[[2'-(2H-tetrazol-5-yl)[1,1'-biphenyl]-4-yl]oxy]-4-quinolinecarboxylic acid, ethyl ester, or a pharmaceutically acceptable salt thereof.

28. A compound of claim 1, 7-Chloro-2-ethyl-3-[[2'-(2H-tetrazol-5-yl)[1,1'-biphenyl]-4-yl]oxy]-4-quinolinecarboxylic acid, or a pharmaceutically acceptable salt thereof.

29. A compound of claim 1, 2-Propyl-3-[[2'-(2H-tetrazol-5-yl)[1,1'-biphenyl]-4-yl]oxy]-4-quinolinecarboxylic acid, 2-(diethylamino)-2-oxoethyl ester, or a pharmaceutically acceptable salt thereof.

30. A compound of claim 1, 2-Cyclopropyl-3-[[2'-(2H-tetrazol-5-yl)[1,1'-biphenyl]-4-yl]oxy]-4-quinolinecarboxylic acid, 2-methyl-1-(1-oxopropoxy)propyl ester, or a pharmaceutically acceptable salt thereof.

31. A compound of claim 1, 2-Cyclopropyl-3-[[2'-(2H-tetrazol-5-yl)[1,1'-biphenyl]-4-yl]oxy]-4-quinolinecarboxylic acid, ethyl ester, or a pharmaceutically acceptable salt thereof.

32. A compound of claim 1, 2-Cyclopropyl-6-methoxy-3-[[2'-(2H-tetrazol-5-yl)[1,1'-biphenyl]-4-yl]oxy]-4-quinolinecarboxylic acid, or a pharmaceutically acceptable salt thereof.

33. A compound of claim 1, 2-Cyclopropyl-3-[[2'-(2H-tetrazol-5-yl)[1,1'-biphenyl]-4-yl]oxy]-4-quinolinecarboxylic acid, 2-methyl-1-(2,2-dimethyl-1-oxopropoxy)propyl ester, or a pharmaceutically acceptable salt thereof.

34. A compound of claim 1, 2-Cyclopropyl-3-[[2'-(2H-tetrazol-5-yl)[1,1'-biphenyl]-4-yl]oxy]-4-quinolinecarboxylic acid, 1-(1-oxopropoxy)ethyl ester, or a pharmaceutically acceptable salt thereof.

35. A compound of claim 1, 2-Propyl-3-[[2'-(2H-tetrazol-5-yl)[1,1'-biphenyl]-4-yl]oxy]-4-quinolinecarboxylic acid, 2-methyl-1-(2,2-dimethyl-1-oxopropoxy)propyl ester, or a pharmaceutically acceptable salt thereof.

36. A compound of claim 1, 2-Ethyl-3-[[2'-(2H-tetrazol-5-yl)[1,1'-biphenyl]-4-yl]oxy]-4-quinolinecarboxylic acid, ethyl ester, or a pharmaceutically acceptable salt thereof.

37. A compound of claim 1, 2-Cyclopropyl-5-methyl-3-[[2'-(2H-tetrazol-5-yl)[1,1'-biphenyl]-4-yl]oxy]-4-quinolinecarboxylic acid, or a pharmaceutically acceptable salt thereof.

38. A pharmaceutical composition comprising an effective amount of a compound of claim 1 and a pharmaceutically acceptable carrier.

39. A method for treating hypertension comprising administering to a mammalian specie in need thereof a therapeutically effective amount of a composition of claim 38.

40. A method for treating congestive heart failure comprising administering to a mammalian specie in need thereof a therapeutically effective amount of a composition of claim 38.

41. A method for treating cardiac hypertrophy comprising administering to a mammalian specie in need thereof a therapeutically effective amount of a composition of claim 38.

* * * * *